(12) United States Patent
Naik

(10) Patent No.: US 10,136,777 B2
(45) Date of Patent: Nov. 27, 2018

(54) STOOL FOR USE WITH A TOILET

(71) Applicant: NadiaLabs, Inc., Sunnyvale, CA (US)

(72) Inventor: Tikeswar Naik, Sunnyvale, CA (US)

(73) Assignee: NadiaLabs, Inc., Sunnyvale, CA (US)

( * ) Notice: Subject to any disclaimer, the term of this patent is extended or adjusted under 35 U.S.C. 154(b) by 0 days.

(21) Appl. No.: 15/177,205

(22) Filed: Jun. 8, 2016

(65) Prior Publication Data

US 2016/0360937 A1    Dec. 15, 2016

Related U.S. Application Data

(60) Provisional application No. 62/344,811, filed on Jun. 2, 2016, provisional application No. 62/323,514, filed
(Continued)

(51) Int. Cl.
*A47K 17/02* (2006.01)
*A47C 16/02* (2006.01)
(Continued)

(52) U.S. Cl.
CPC ............ *A47K 17/028* (2013.01); *A45D 34/02* (2013.01); *A47C 16/02* (2013.01); *A47C 16/025* (2013.01); *A61B 5/1036* (2013.01); *A61H 23/02* (2013.01); *A61L 9/00* (2013.01); *G01G 19/52* (2013.01); *G08C 17/02* (2013.01); *A61H 15/0078* (2013.01); *A61H 2015/0007* (2013.01); *A61H 2015/0014* (2013.01); *A61H 2015/0028* (2013.01); *A61H 2015/0042* (2013.01); *A61H 2201/0107* (2013.01); *A61H 2201/0161* (2013.01); *A61H 2201/0188* (2013.01); *A61H 2201/0192* (2013.01);
(Continued)

(58) Field of Classification Search
CPC ...... A47K 17/028; A47K 17/02; A47C 16/02; A47C 16/025
USPC .............................................. 4/254
See application file for complete search history.

(56) References Cited

U.S. PATENT DOCUMENTS 4,175,294 A * 11/1979 Boyd ...................... A47K 13/24
4/234
4,979,240 A * 12/1990 Welles .................... A47K 17/00
4/254
(Continued)

FOREIGN PATENT DOCUMENTS

DE    2220156 A1    11/1973
EP    0682906 A2    11/1995
(Continued)

OTHER PUBLICATIONS

The International Search Report for International Application No. PCT/US2016/036642, dated Sep. 8, 2016.
(Continued)

*Primary Examiner* — J. Casimer Jacyna
(74) *Attorney, Agent, or Firm* — Brett A. Schenck

(57) ABSTRACT

A stool is provided that provides a raised heel squat position to a user that engages the stool. The raised heel squatting position promotes a healthy and productive experience on a toilet. The stool may be collapsible for easier storage and transportation. The stool may be adjustable to provide custom fittings to different size users. Additionally, the stool may be intelligent and may provide a customized immersive experience to a person on a toilet.

16 Claims, 21 Drawing Sheets

Related U.S. Application Data on Apr. 15, 2016, provisional application No. 62/297,864, filed on Feb. 20, 2016, provisional application No. 62/276,816, filed on Jan. 8, 2016, provisional application No. 62/246,107, filed on Oct. 25, 2015, provisional application No. 62/222,507, filed on Sep. 23, 2015, provisional application No. 62/190,260, filed on Jul. 9, 2015, provisional application No. 62/173,338, filed on Jun. 9, 2015.

(51) Int. Cl.

| | |
|---|---|
| *G01G 19/52* | (2006.01) |
| *A45D 34/02* | (2006.01) |
| *A61H 23/02* | (2006.01) |
| *A61B 5/103* | (2006.01) |
| *A61L 9/00* | (2006.01) |
| *G08C 17/02* | (2006.01) |
| *A61H 15/00* | (2006.01) |
| *A63B 71/06* | (2006.01) |
| *A63B 23/04* | (2006.01) |
| *A63B 21/00* | (2006.01) |

(52) U.S. Cl.
CPC ........... *A61H 2201/0207* (2013.01); *A61H 2201/0214* (2013.01); *A61H 2201/0221* (2013.01); *A61H 2201/164* (2013.01); *A61H 2201/1685* (2013.01); *A61H 2201/503* (2013.01); *A61H 2201/5007* (2013.01); *A61H 2201/5012* (2013.01); *A61H 2201/5038* (2013.01); *A61H 2201/5043* (2013.01); *A61H 2201/5048* (2013.01); *A61H 2201/5058* (2013.01); *A61H 2201/5097* (2013.01); *A61H 2203/0431* (2013.01); *A61H 2205/12* (2013.01); *A61H 2205/125* (2013.01); *A61H 2230/00* (2013.01); *A61H 2230/06* (2013.01); *A61H 2230/202* (2013.01); *A61H 2230/25* (2013.01); *A61H 2230/30* (2013.01); *A61H 2230/50* (2013.01); *A61H 2230/70* (2013.01); *A61H 2230/80* (2013.01); *A63B 21/00047* (2013.01); *A63B 23/0458* (2013.01); *A63B 71/0622* (2013.01); *A63B 2023/0411* (2013.01); *A63B 2071/0625* (2013.01); *A63B 2071/0655* (2013.01); *A63B 2210/50* (2013.01); *A63B 2225/093* (2013.01); *A63B 2225/50* (2013.01); *A63B 2225/64* (2013.01); *A63B 2225/66* (2013.01); *A63B 2230/01* (2013.01); *A63B 2230/08* (2013.01); *A63B 2230/202* (2013.01); *A63B 2230/30* (2013.01); *A63B 2230/50* (2013.01); *G08C 2201/93* (2013.01)

(56) References Cited

U.S. PATENT DOCUMENTS

| | | | |
|---|---|---|---|
| 6,442,779 B1 | 9/2002 | Levert et al. | |
| 6,651,262 B1* | 11/2003 | Tinsley | A47K 13/10 4/246.1 |
| 8,344,272 B1* | 1/2013 | Goldberg | A47C 31/126 177/126 |
| 2009/0145340 A1* | 6/2009 | Parvizian | A47C 16/02 108/137 |
| 2010/0251469 A1* | 10/2010 | Kim | A47K 17/024 4/254 |
| 2013/0048428 A1 | 2/2013 | Chancler | |
| 2013/0174337 A1* | 7/2013 | Fagre | A47K 17/028 4/254 |
| 2013/0345609 A1* | 12/2013 | Miller | A61H 15/00 601/120 |
| 2014/0123376 A1* | 5/2014 | Edwards | A47K 17/028 4/254 |
| 2015/0113719 A1* | 4/2015 | Good | A47K 17/028 4/254 |
| 2015/0272410 A1* | 10/2015 | Lavassani | A47K 17/028 4/254 |
| 2015/0327740 A1 | 11/2015 | Edwards et al. | |

FOREIGN PATENT DOCUMENTS

| | | | | |
|---|---|---|---|---|
| JP | 7-236596 | * | 9/1995 | ........... A47K 17/028 |
| JP | 2003-293422 | * | 10/2003 | |
| JP | 2003-339671 | * | 12/2003 | |
| JP | 2004-337225 | * | 12/2004 | |
| JP | 2007-330460 | * | 12/2007 | ........... A47K 17/028 |
| KR | 10-2012-0138260 A | | 9/2012 | |

OTHER PUBLICATIONS

The Written Opinion of the International Searching Authority for International Application No. PCT/US2016/036642, dated Sep. 8, 2016.

2-in-1 iPotty with Activity seat for iPad. Datasheet (online). CTA Digital, Jul. 5, 2014 [retrieved via www.archive.org on Dec. 20, 2017]. Retrieved from internet http://www.ctadigital.com/item.asp?item=3016.

* cited by examiner

STOOL FOR USE WITH A TOILET

CROSS-REFERENCE TO RELATED APPLICATIONS

This application claims the priority benefit of U.S. provisional patent application Ser. No. 62/173,338, titled "EASY RELEASE POTTY FOOT-STOOL AND/OR OTHER INVENTIONS," filed Jun. 9, 2015, the priority benefit of U.S. provisional patent application Ser. No. 62/190,260, titled "EASY RELEASE POTTY FOOT-STOOL AND/OR OTHER INVENTIONS," filed Jul. 9, 2015, the priority benefit of U.S. provisional patent application Ser. No. 62/222,507, titled "FOOTSTOOL AND OTHER WELLNESS PRODUCTS," filed Sep. 23, 2015, the priority benefit of U.S. provisional patent application Ser. No. 62/246,107, titled "FOOTSTOOL AND OTHER INVENTIONS," filed Oct. 25, 2015, the priority benefit of U.S. provisional patent application Ser. No. 62/276,816, titled "FOOTSTOOL AND OTHER INVENTIONS V6," filed Jan. 8, 2016, the priority benefit of U.S. provisional patent application Ser. No. 62/297,864, titled "FOOTSTOOL AND OTHER INVENTIONS V7," filed Feb. 20, 2016, the priority benefit of U.S. provisional patent application Ser. No. 62/323,514, titled "FOOTSTOOL AND OTHER INVENTIONS V8," filed Apr. 15, 2016, and the priority benefit of U.S. provisional patent application Ser. No. 62/344,811, titled "FOOTSTOOL AND OTHER INVENTIONS V9," filed, Jun. 2, 2016, the disclosures of which are incorporated herein by reference.

BACKGROUND OF THE INVENTION

People perform regular bowel movements as part of a healthy lifestyle. In Western civilization, most people sit on toilets to perform a bowel movement. The posture required to sit on a typical western civilization toilet creates a kink in the colon that hinders the flow of bowel movements, making it difficult to complete a bowel movement. This can lead to many health issues like constipation, hemorrhoids, and other colon diseases.

Existing foot stools do not improve the experience of a bowel movement. Most stools have a flat design which requires the entire foot to be lifted to the top of the stool, which may not be comfortable for those having a body that is not flexible, such as for example elderly people or even possible by many people, such as for examples people whose body are not that flexible, elderly people, and people with joint pains.

SUMMARY OF THE CLAIMED INVENTION

A stool is provided that allows a user to sit in a raised heel squat position. The stool may be used by people having different heights and foot size, and allows for easy squat intensity adjustment. The raised heel squatting position provided by the stool promotes a healthy and productive bowel movement while on a toilet. The stool may be static or intelligently dynamic, include a massaging unit, and incorporate intelligent features to provide a customized immersive experience to a person on a toilet.

In an embodiment, the stool may include a platform, ramp, and base portion. The platform can receive a portion of the bottom of a user's feet. The ramp can extend upward and away from the platform, the ramp extending away from the platform at a first angle. The ramp and platform can have a width suitable to receive both feet of a user sitting on a toilet. The base portion supports the platform and ramp. The stool can have a back side that is curved to allow the stool to be positioned against a curved toilet bowl.

DETAILED DESCRIPTION

A squatting position by a user of a toilet promotes a healthy bowel movement. Unlike a squatting position, attempting a bowel movement in a sitting posture can create a kink in a user's colon that hinders a bowel movement. An upright sitting position can lead to many health issues, including but not limited to constipation and hemorrhoids. Thus, while a western toilet offers the comfort, sitting on a typical toilet is not conducive to a productive and healthy bowel movement.

A stool is provided that allows a user to squat in a raised heel squat position, as well as adjust the squat intensity easily. The raised heel squatting position is supported by the structure and features of the stool and promotes a healthy and productive bowel movement. The stool may be static or dynamically intelligent, include a massaging unit, and incorporate intelligent features to provide a customized immersive experience to a person on a toilet.

A squatting posture, as opposed to a sitting position, opens up the colon for a clean and healthy bowel movement. Existing toilet foot stools exist for use with a western toilet, though they are very limited in terms of functionality and utility, and do not improve the overall bathroom experience.

Foot Stool

The stool disclosed herein may include a base portion that may include a solid base or one or more legs for supporting the stool, a platform, and a ramp portion. The platform and ramp portion support portions of a user's foot. In some instances, the platform and ramp portion may support a user's foot to a position elevated from the floor, and optionally keep the heel raised above the toes of the user's foot. The stool may also include a massage unit and one or more sensors, input and output components, a controller and/or processor for processing input and generating output, and other components described herein.

Figure 1A:
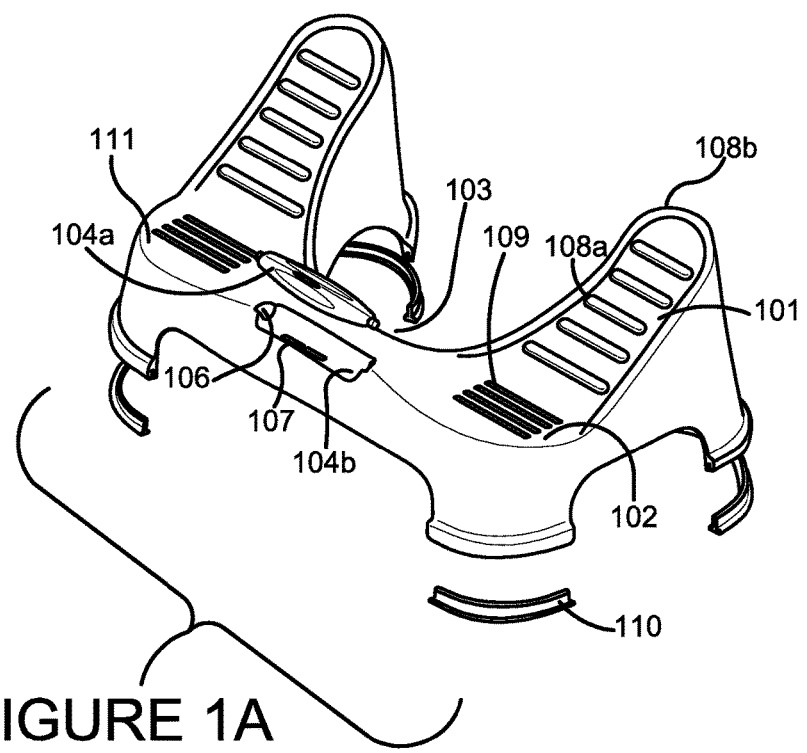
FIG. 1A illustrates a perspective view of an exemplary stool.
Figure 1B:
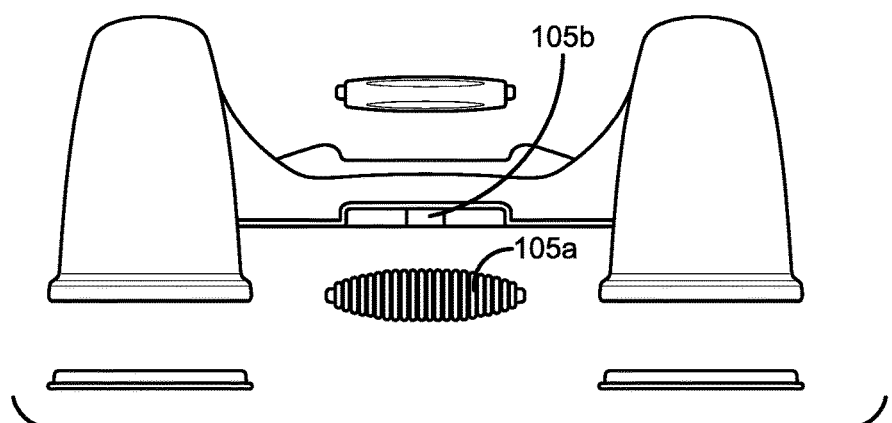
FIG. 1B illustrates a back view of an exemplary stool.
Figure 1C:
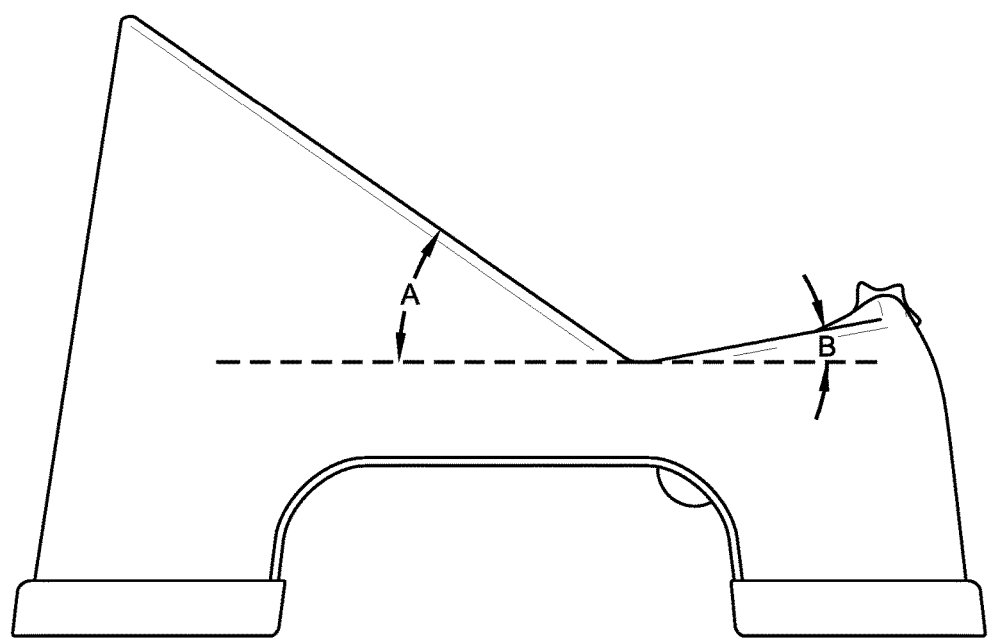
FIG. 1C illustrates a side view of an exemplary stool.

FIGS. 1A, 1B, and 1C illustrate an exemplary stool. The stool disclosed in FIGS. 1A-C includes a ramp portions 101, platform 102, a toilet confirming edge 103, a modular and detachable massage unit 104a and holder 104b, a spare massage unit 105a and holder 105b, and a mechanism 106 to secure the massage unit. The ramp portions may each be at an angle A with respect to a horizontal plane, such as for example an angle of about 15 degrees, 20 degrees, 30 degrees 35 degrees, or some other angle with respect to a horizontal plane. In some implementations, ramp 101 (e.g., two ramp portions, a first portion for one foot and a second portion for a second foot, collectively forming the ramp) may engage the heel of a user's foot (i.e., the rear underside of the user's foot) and the mid-portion of the user's foot. For example, a user's heel may engage the top of the ramp and the sole of a user's foot.

Platform 102 may be coupled to ramp 101 and have a surface which is relatively flat. In some instances, the platform may be at a slight angle with respect to a horizontal plane, such as for example an angle B of about 5, 10, 15, or 20 degrees from horizontal. Platform 102 may engage an upper portion and/or the toes of the user's foot. In some implementations, a user's toes may be positioned on the platform while the ball of the user's foot may rest on the ramp. When the user's toes engage or rest upon the platform and the user's ball of rear portion of the foot engages or rests upon the ramp, the foot will be positioned in a declined position (such that the front of the foot is lower than the back of the foot), thereby providing a comfortable squatting position.

In some instances, the surface of the platform may be angled at an angle B such that the toes of the user, when the ball of the foot is on the ramp, are angled slightly upward with respect to a horizontal plane.

The exemplary stool of FIGS. 1A-C may also include liquid drainage holes 107, ramp traction elements 108a-b, platform traction elements 109, leg pads 110, and hump 111. Liquid drainage holes 107 may be provided in the platform portion of the stool to allow pooled liquid to drain through the material of the stool. The liquid drainage holes may allow for easier cleaning and drying of the stool.

Ramp traction elements 108a-b may include elements that provides traction for the bottom of a user's foot that engages the surface of the ramp. The ramp traction elements 108a-b may include vertical strips 108a (illustrated in FIG. 1A), bumps, or other vertically raised portions that extend from the ramp. The ramp traction elements may include one or more patches of non-slip coating or materials that prevent a user's foot from slipping when the bottom of the foot engages the surface of the ramp, without requiring a vertical extension from the surface of the ramp. The ramp traction element may also include a ramp edge traction element 108b that provides traction to a user's foot on the edge of the ramp.

Platform traction elements 109 may include an element that provides traction for the bottom of a user's foot, such as the bottom of the user's toes, which engages the surface of the platform. Similar to ramp traction elements 108a-b, the platform traction elements 109 may include vertical strips, bumps, or other vertically raised portions that extend from the platform, and/or may include one or more patches of a non-slip coating or material that prevent a user's foot from slipping when engaging the surface of the platform. In some instances, the platform traction elements 109 can be coarse, which traps less dirt and helps with easy cleaning.

The base of the stool may include the portion of the stool below the upper surface of the ramp and the upper surface of the platform. The base of the stool may include a surface that engages a floor or other surface underneath the stool. The base portion, in some implementations, may include any material or parts between the bottom surface of the legs and the lower edges of the ramp and platform, such as the vertical and other non-horizontal surfaces and material between the platform surface and the stool legs. In some instances, the base of the stool may include one or more legs, such as for example four legs (illustrated in FIG. 1A), or a portion that extends beyond one or more legs and makes contact with a floor. The one or more legs, or extended portion, may include leg pads 110. Leg pads 110 may be of a non-slip or slip resistant material, such as for example rubber, which will not slip on the dry or wet floor. By preventing slipping, the leg pads 110 help keep the stool in place when a user gets on and off the stool, or during the usage of the stool.

The platform 102 may include a hump 111. The hump may be used to keep a user's legs in a squatting position, and can easily allow for a user's feet to move forward or backward (using the hump to provide support and traction to the bottom of the feet). When a user move's the feet forward or backward over the hump, it will change the foot angle and corresponding squat intensity (see FIG. 5). Hump 111 may include a bridge or other extension that extends away from platform 102. In some implementations, hump is a vertical ridge with a curved top that extends vertically from platform. The hump may help keep user's foot in place on the stool, may provide a feature that allows a user to move the stool forward and backward using the user's toes, and may otherwise engage a user's foot.

Unlike a flat-top footstool, the ramp design provides a unique advantage in that one can simply move the feet forward or backward to change the squat intensity. A user of the stool may move the heels forward and place the user's toes over the edge of the platform (see FIGS. 5b-c). While moving the heels forward and backward along the ramp to adjust the squat intensity, the elements 108a can provide traction and support for the ball (or heel, the rear part of the foot). Sitting on the toilet sometimes reduces blood circulation, and can cause numbness in the legs. Providing a stool that allows for an easy and comfortable transition between a raised heel squatting position (see FIG. 5a, with heels up on the ramp 101 and toes on the platform 102) and less intense squatting position (see FIG. 5b, with heels down the ramp and toes slightly over the edge of the platform) or even a relatively flat foot gentle-squatting/sitting position (see FIG. 5c, with heels on the platform 102 and toes over the edge of the hump) can be very useful and beneficial to user comfort while performing a bowel movement.

An exemplary stool may include a massage unit integrated or coupled to the platform. The massage unit may be static and passive or dynamic. When implemented passively, a massage unit may include a rolling massage 104a with one or more ridges, bumps, balls, or other extensions. The passive massager 104a massage unit may be coupled or integrated into the platform 102 such that it may rotate in response to force applied by the foot of the user. Hence, user may place his or her foot on massager, the massager will roll thereby applying ridges, balls, or other tactile portions to engage the bottom of the user's foot, thereby providing a massage to the user. The massager may be replaceable, and spare massage units may be stored at one or more locations within the stool.

A snap-fit mechanism can be implemented (106) to secure the massage unit (104*a*) to keep it in place. The snap fit mechanism may include a hole 106 that receives an end of the massager 104*a*, but other securing mechanisms can also be implemented (for example, detachable bushings or connectors).

In some implementations, instead of placing the massager unit at the center (104*a* and 104*b*), there can be separate massager units for each feet in front of the respective toes areas. A spare massager can also be stored at a different location (105*a-b*, or behind the back feet for example). Different mechanisms may be used to store and/or attach a spare massager in the spare holder. For example, the spare holder can include a through hole in the massager 105*a* that the attachment 105*b* inserts and/or fits into. In some implementations, one or more magnets can be used to implement the storage mechanism. In one case one massager unit can be long enough to span across the entire width of the footstool (covering both the toes areas). In one case there can be array of massagers on the toe-platform or the heel platform.

In some implementations, massage unit 104*a* can include battery operated massager with logic to control massage patterns, intensity, duration, and other aspects of massage. In some implementations, the logic may be implemented remotely in a mobile application, stored and executed on a mobile device which may communicate directly or indirectly with the stool and massage unit (see FIG. 14). The massager may include a roller, a series of beads or balls, a combination of these forms, or other forms. For example, in one case it may be just a fixed unit that does not roll, but includes a vibrating massage sub-units controlled by local or remote logic.

In some implementations, the massager 104*a* can administer massage based on preference, needs or past massage history for a particular user. For example, user massage preferences and history may be stored for a particular user, such as in an account stored on a remote database. When a user on the stool is identified, either automatically based on user foot print, weight, or other bio sensor, or by login credentials provided to a mobile application or the stool itself (e.g., via voice recognition), the user's stored massage history and preferences may be retrieved. Similarly, past history and user preferences for acupressure or other foot therapies may be stored in a user account and applied to the user upon detecting and validating the particular user on the stool.

Targeted massage patterns or foot therapy for a specific purpose can be applied to the feet by the stool massager 104*a*. For examples, preprogrammed massage patterns for stress relief, easier bowel movement, memory improvement, and other purposes may be applied based on user input provided to the stool, for example through input devices built into the stool, input devices added to the stool at the massager holder 104*b*, or through a mobile application on a mobile device in communication with the stool. A feedback based massage pattern for foot therapy can be provided, and based on how the user responds to specific massage or therapy, the massaging can be adjusted. In one case the massager can automatically sense when a foot is placed on it and may start applying a massage. Similarly, as soon as a foot is removed from the stool, the foot massage may stop. In some implementations, when the massager is implemented electronically, the massager may apply a massage to a user when the user applies pressure to the massager, when the stool receives a request to provide a massage to the user, based on sensor data provided by sensor to a processor incorporated within the stool, or based on other events. The massager may include rotating or oscillating cylinders, vibrating spheroidal surfaces, and other shapes.

The stool may include a variety of massages of different shapes and in different locations. For example, a massager 104*a* can include a vertically mounted rollable cylinder (to massage the bottom of the feet), a horizontal rollable disk/cylinder (to massage the sides of the feet), a surface contour (to mimic a stone, rocky surface, etc.), or a natural element patch (e.g., a grassy patch, a heat pad/patch, therapeutic patch, etc.). Each massage unit may be smart in that it is connected to logic that controls the massager based on one or more inputs or logical rules, and can be connected to and controlled by a remote device, such as a mobile device executing an application that communicates and controls the stool and massage unit. These units can also integrate therapeutic sub-elements that can be personalized to a particular user. The massage units can also be 'intelligent' to know and understand the user and self-adjust appropriately, and send valuable health/fitness/emotional state feedback to the mobile device and or the cloud.

In some embodiments, a vertical surface of the stool may be shaped to accommodate a vertical surface of a toilet. For example, the rear vertical surface 103 of the stool may be curved to accommodate the front curved surface of a toilet base. This conforming vertical surfaces of the stool and toilet allow the stool to be placed up against the toilet for storage and out of the way when not in use.

The ramp design of the stool disclosed herein provides several advantages. The ramp design allows for easy loading and use because of the slanted position of the foot provided by the ramp (resulting in a lower height of the toes platform). The ramp design also allows different height users, and different size feet and toilet, to be supported by the stool described herein, allowing the stool to be a "one size fits all." It also makes it possible to adjust the squat intensity easily just by moving the feet forward or backward (no cumbersome mechanisms involved and no tool required). Furthermore, the ramp and platform combination allow for different foot positions, allowing people in different dispositions to use the stool, including elderly people, not so flexible people, pregnant woman, and active healthy people. It also makes it possible and practical to integrate a massage element and/or other technology elements. Additionally, because the stool includes a massaging element, any stigma for purchasing a stool and storing the stool in the bathroom purely to assist with bowel movements is eliminated, as the present stool may be considered a massaging or technology stool for use in the bathroom, or even while sitting on a chair, despite having several benefits that promote healthy bowel movements.

Further advantages include the static rollable massager unit (pictured in FIG. 1A) allowing for different massagers 104*a* to be interchanged within the massaging unit, which includes the receiving mechanism 106 and massage support portion 104*b*. In addition to a massager 140*a*, the massager unit may receive other attachments, including sensors and actuators, input and output devices, computing elements and components, and other devices that provide for a smart stool.

Since the squat intensity can be adjusted simply by moving the feet forward or backward, it also works for family members who have different heights and/or squatting needs, without having to keep multiple-height footstools. The adjustable-squatting is gentler on joints for those who have health issues or otherwise. This also helps one get adjusted to squatting slowly, for example if a particular user has not used the stool or practiced a squat position previously. The various humps and bumps (108a-b, 113) on the surface can also serve as passive massager that a user can place the feet on top and rub.

Foot Stool Use Positions

A user of a western toilet typically places their feet on the ground or floor while using a toilet. When using the foot stool of the present disclosure, placing the feet on the footstool can raise the knees above the hip, thereby mimicking a squatting posture. This offers the benefit of squatting at the comfort of western toilet. The ramp design of the foot stool of the present disclosure not only helps achieve the squatting posture, but also offers other advantages that are not possible with a flat-top design.

Figure 2:
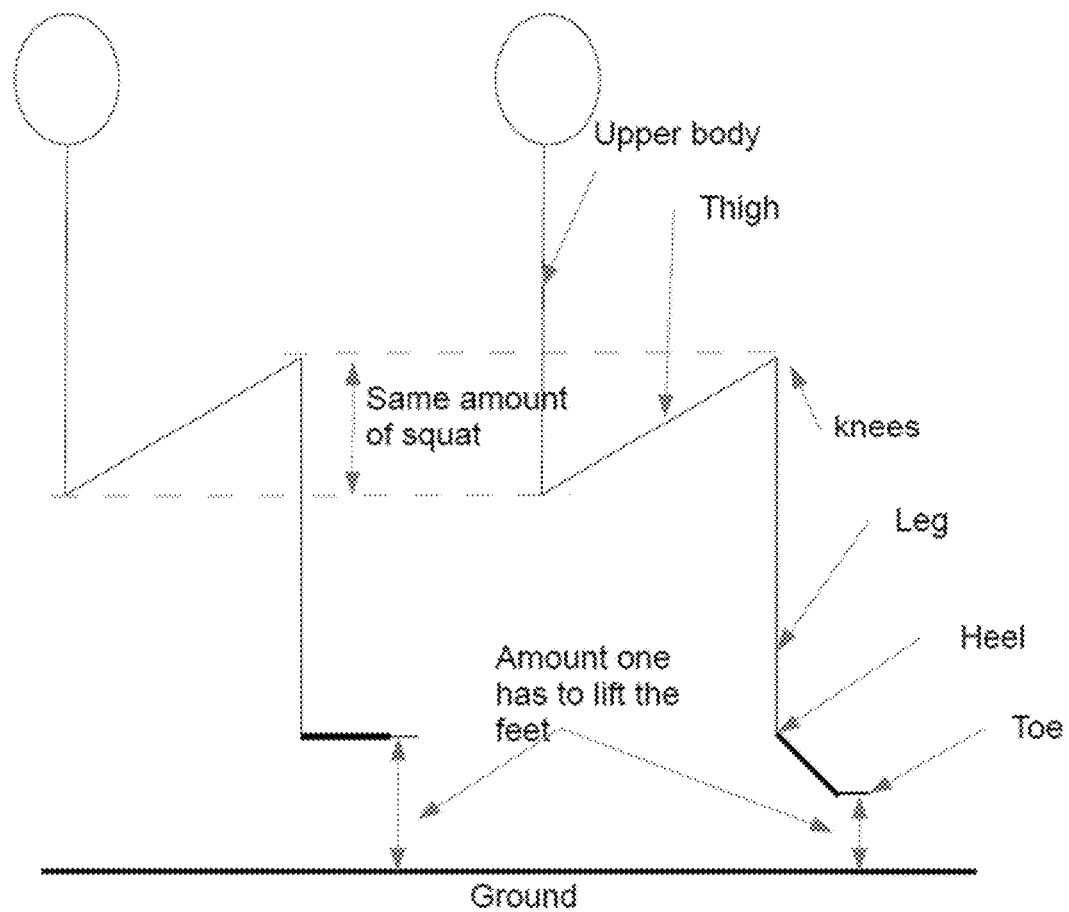
FIG. 2 illustrates a comparison of a person sitting on a platform with a stool of the prior art and a person sitting on a platform using the stool of the present technology.
Figure 3A:
FIG. 3A illustrates a person squatting flat-footed.
Figure 3B:
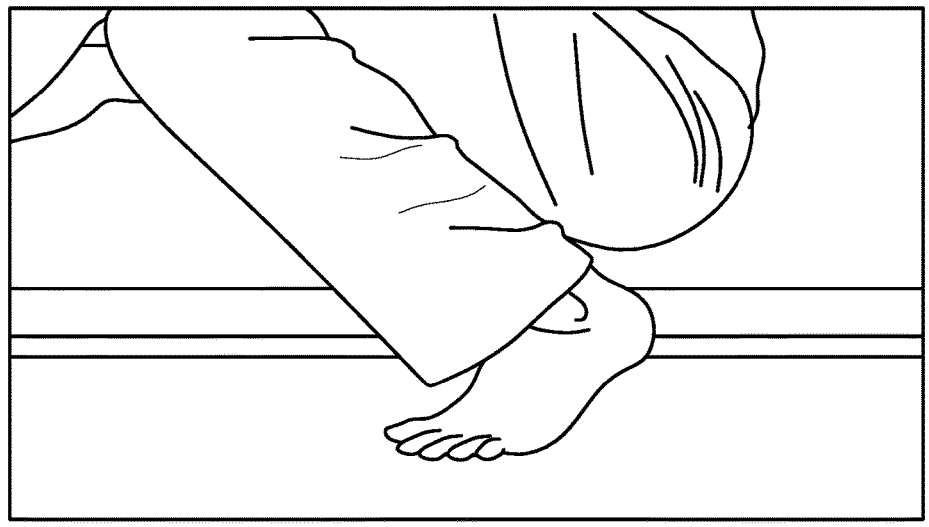
FIG. 3B illustrates a person squatting with raised heels.

FIG. 2 illustrates a comparison of a person sitting on a platform with a stool having a purely flat platform and a person sitting on the stool having a ramp and platform. To achieve a squatting position, the user can either lift the entire foot to the desired height, or just raise the heels and then lift the feet slightly to achieve the same squatting effect (see FIG. 2). The latter (raised heel as opposed to lifting the feet) is much easier for a user and provides a more comfortable rest position than having the feet rest on a flat platform while squatting. Squatting, in general, is a lot easier and more comfortable with raised heels (see FIGS. 3A-B).

Figure 4:
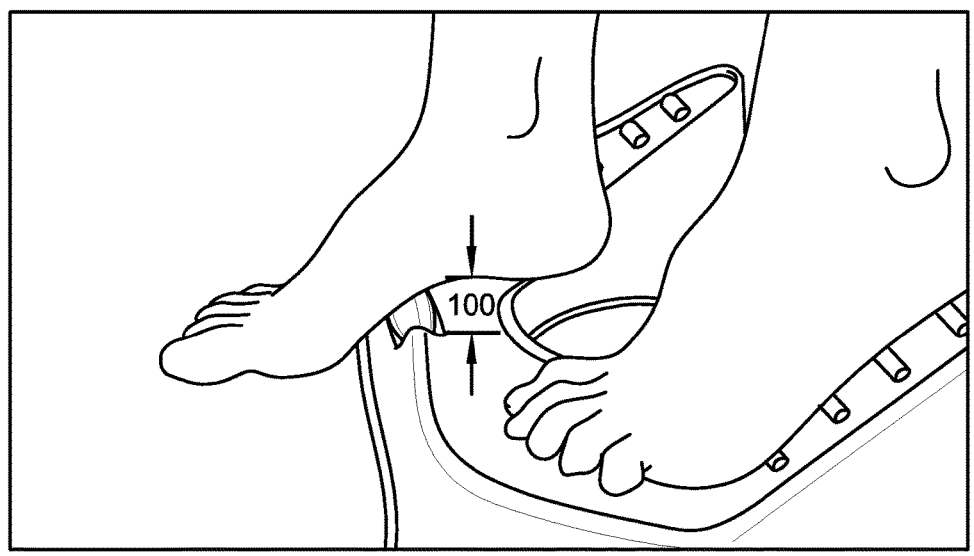
FIG. 4 illustrates a level of clearance between a stool and the bottom of the user's foot when the user engages the stool massage.

FIG. 4 illustrates a level of clearance between a stool and the bottom of the user's foot when the user engages the stool massage. Due to the slight angle in the platform, a clearance 400 is created that allows a user to easily move his or her foot back and forth across the massager.

Figure 5C:
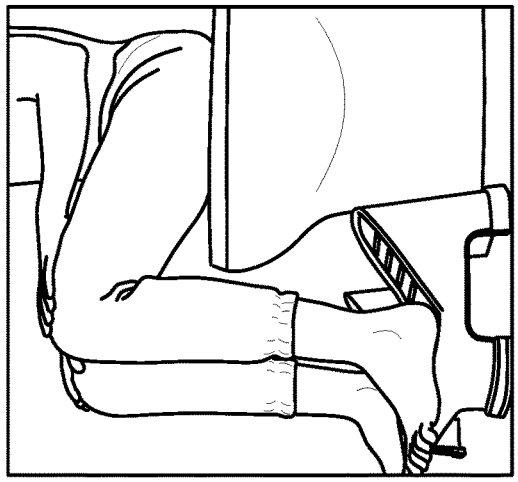
FIGS. 5A-C illustrate a user at different squatting positions on an exemplary stool.
Figure 5B:
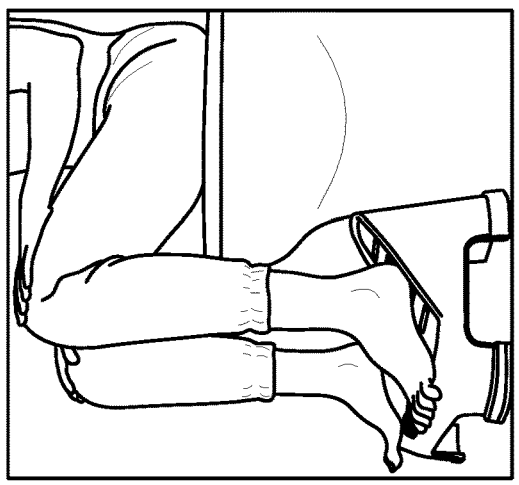
Figure 5A:
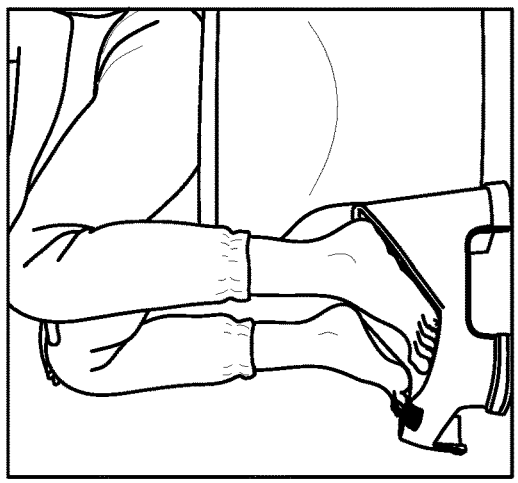

FIGS. 5A-C illustrate a user at different positions on an exemplary stool. A user may position his or her feet such that the toes are engaging the platform and the heels are on the ramp (FIG. 5A). A user may also position his or her feet such that the toes are extended over the edge of the platform and the heels are a bit lower on the ramp (FIG. 5B). A user may also position his or her feet such that the heels are positioned on the platform and the toes are extended past the edge (FIG. 5C).

Figure 6:
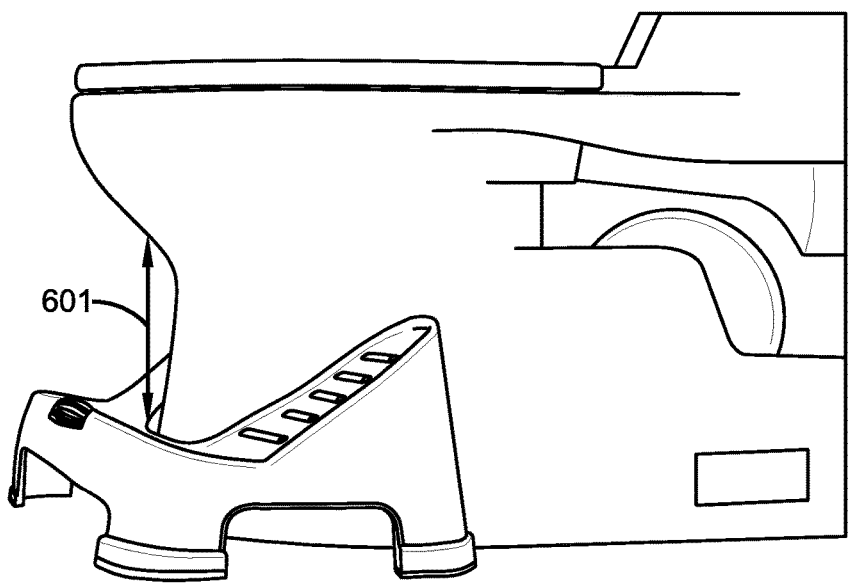
FIG. 6 illustrates a clearance between a platform and a toilet.

The ramp design lends itself to technology integration in a way that is not possible with a flat top footstool. Because of the lower height of the platform portion on the stool described herein, there is enough clearance and space 601 between the platform and the toilet bowel (see FIG. 6) to conveniently integrate any smart elements and access those elements easily and conveniently.

Collapsible Foot Stool

Figure 7A:
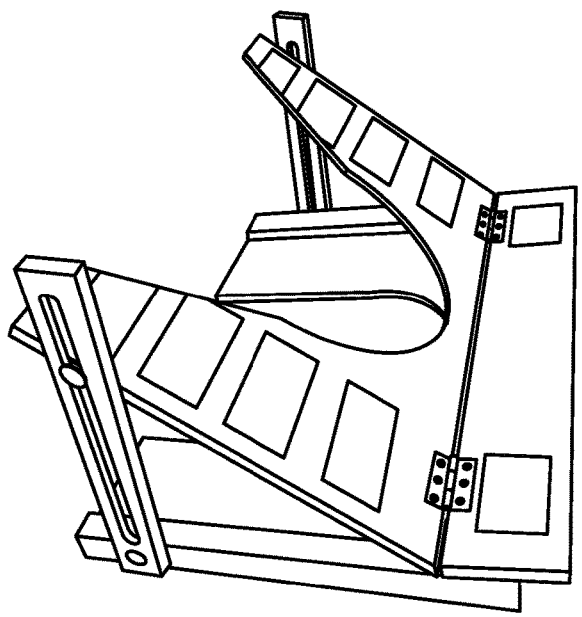
FIGS. 7A-D illustrate a collapsible stool.
Figure 7B:
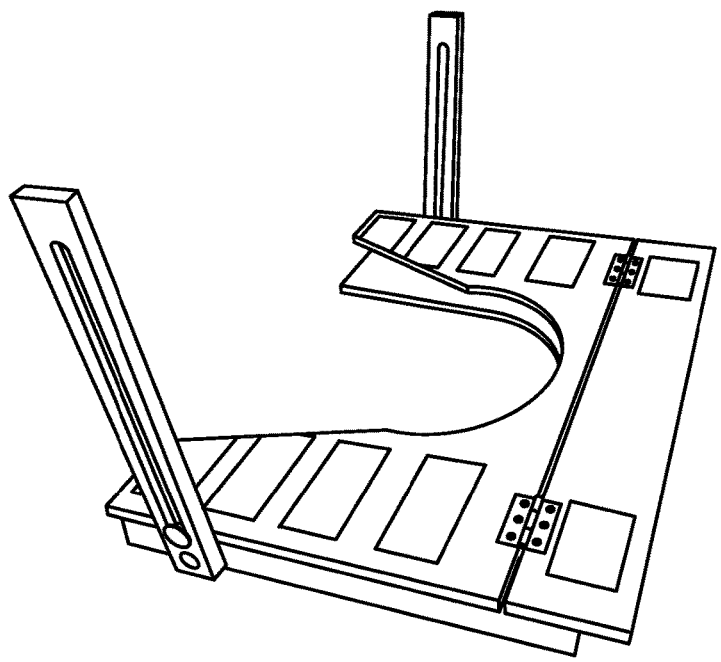
Figure 7C:
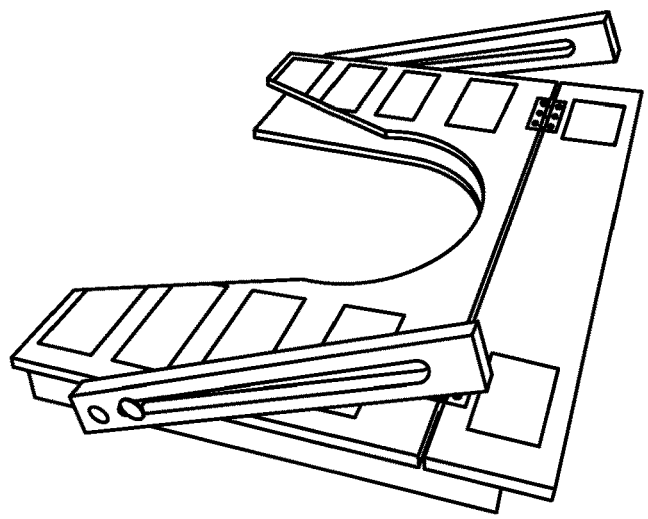
Figure 7D:
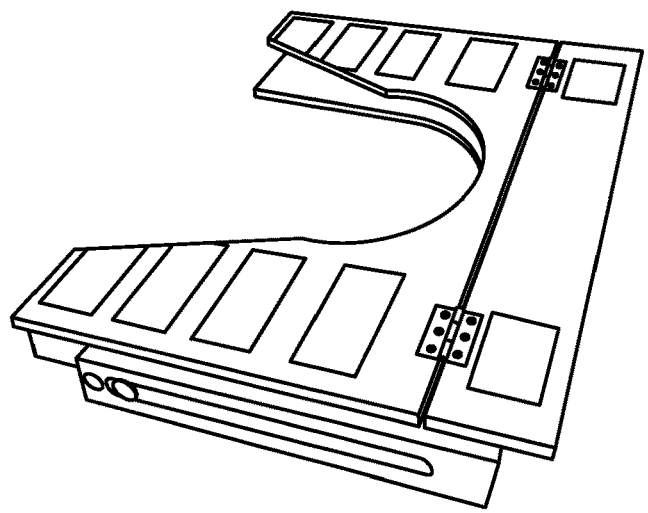

FIGS. 7A-D illustrate an exemplary collapsible stool. In one case the footstool can be easily foldable, making it compact for storage and travel. FIG. 7A illustrates an exemplary collapsible stool that is fully open. The opened collapsible stool includes a ramp and platform, as well as traction portions on the ramp and platform. The ramp is held in place by a pair of support arms that extend from the base of the stool to the ramp. FIG. 7B illustrates an exemplary collapsible stool wherein the ramp is lowered to a horizontal position. Once the ramp is lowered, the support arms of the collapsible stool may be lowered such that the upper end of the support arms move towards the platform of the collapsible stool (FIG. 7C). Once the support arms are completely folded down, the collapsible stool is complete collapsed and may be easily stored (FIG. 7D). In general, graduated slots can be used for height and angle adjustments for the open/un-folded state.

Figure 8A:
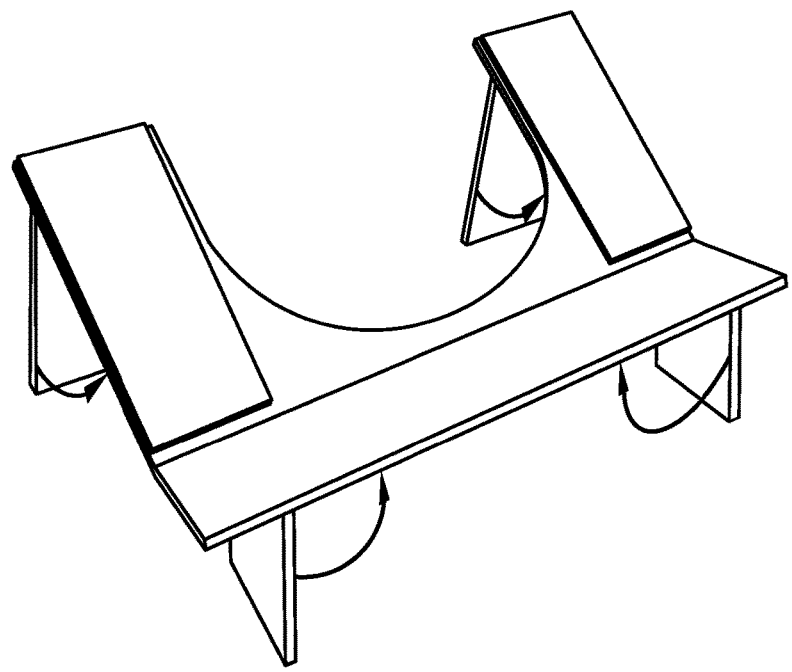
FIGS. 8A-E illustrate another exemplary collapsible stool.
Figure 8B:
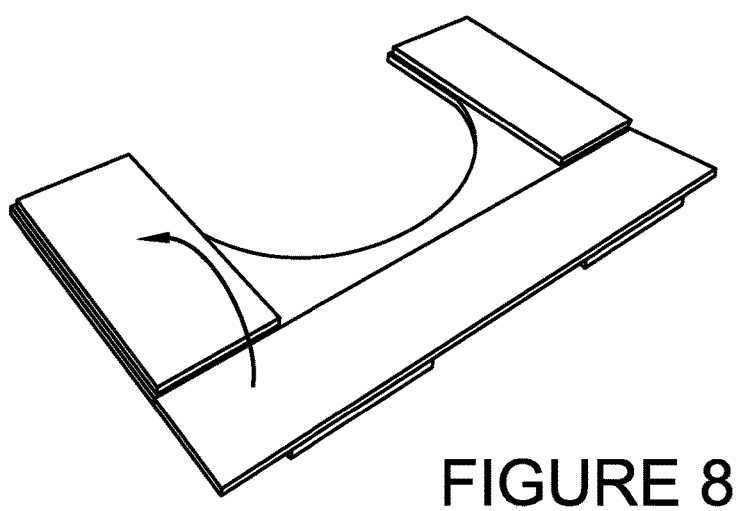
Figure 8C:
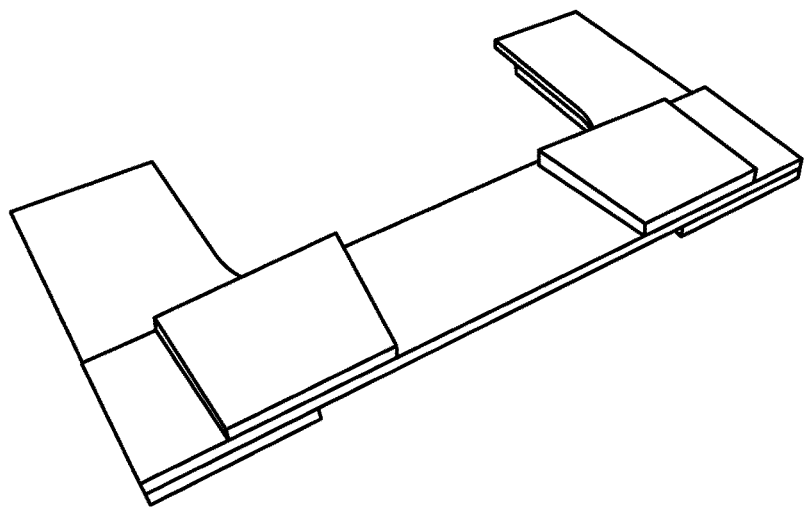

FIGS. 8A-E illustrate another exemplary collapsible stool. FIG. 8A illustrates an exemplary collapsible stool that is fully open. The opened collapsible stool includes a ramp, a platform, and four legs. The ramp and platform are held in place by four legs (two in the front and two in the back) that are foldable. FIG. 8B illustrates the exemplary collapsible stool wherein the four legs are folded to a horizontal position. Once the legs are folded, the platform together with the two front legs may be folded again on top of the already folded ramp (see FIG. 8C). The folded stool (FIG. 8B and 8C) takes up less space than a non-foldable stool and is convenient for storage or travel.

Figure 8D:
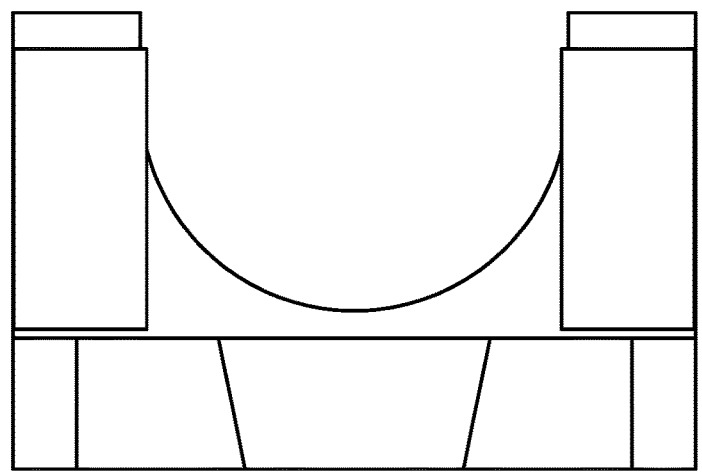

FIG. 8D shows the bottom view of FIG. 8B. In FIG. 8B, the folded legs are outlined. The front leg may be trapezoid shaped (as opposed to a perfect rectangle) that gives a tilt to the platform when the stool is fully open (and place on the floor). The legs may be of different shapes (as opposed to quadrilaterals) or sizes that help with stability and foldability of the stool. The legs can have rubber or other feet pads for traction. The platform can have holding mechanisms for a massage roller or other attachments.

A foldable bracket may be used to secure the ramp and the platform in place for stability in the fully open state (FIG. 8A). The foldable bracket can be placed on the side (near the junction of the ramp and the platform). In one case the front legs can have one more extenders at the base to make the feet wider towards the ramp, as shown in FIG. 8D, and to improve the stability in the fully open state. Other mechanisms also can be used for stability of the stool structure in the fully open state.

Hinges or other mechanisms may be used to provide the folding of folding chair of FIGS. 8A-E. Recessions can be made on the bottom surface of the ramp and the platform such that, when the legs are folded, they store partially or fully inside the recession (making the collapsed state even more compact). In some implementations, small and/or tight hinges (like how a laptop screen is attached to the base) may be made utilized in the collapsible stool. In some implementations, magnets that can be used to hold the legs in place in the folded or unfolded/fully-open positions (so that when one lifts the stool off the ground the legs stay in place either in folded or unfolded state).

Sheet materials having a thickness that provides for a stable stool in the open position can be used for the ramp, platform, and the legs. The hinged edges can be appropriately modified for strength and stability. The legs can be made from different materials and thickness than the ramp or the platform. The ramp, platform, and/or the legs can be made from pipe, tube, corrugated material, c-channel, etc. In one implementation, the ramp and/or platform can have a solid frame and include a mesh connected to the frame material to provide the surface of the stool, which can make the stool lighter. In some implementations, one or more legs of the collapsible stool may be telescopic legs that can be used for height and angle adjustments in the open/un-folded state.

Figure 8E:
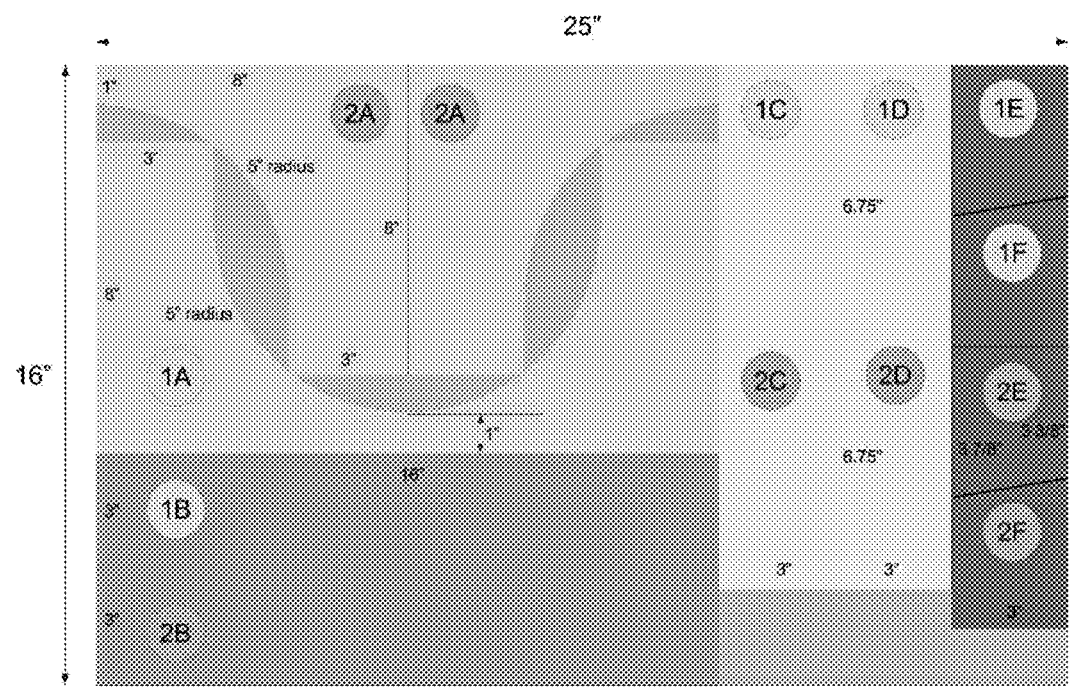

In some implementations, the sheet material may be used to make the parts of the collapsible stool (FIG. 8A). When sheet material is used, FIG. 8E shows the layout and exemplary dimensions the different parts can be arranged to make two quantity of the collapsible stool from a single rectangular sheet material with minimal material wastage (it is understood that machining/cutting tolerance needs to be included between the parts depending on the cutting technology used). In FIG. 8E, A refers to the ramp, B the platform, C and D the back legs, E and F the front legs, and 1 and 2 denote the two units that can be made from the rectangular sheet. The leftover materials can be used to make a wedge and/or feet extension for stability of the stool in fully open state. The particular shape and design of the collapsible stool is intended to be exemplary Different manufacturing methods may be used to make some or all parts of the collapsible foot stool, and the collapsible stool described herein is intended to include other variations of a collapsible stool.

In some instances, the footstool can be made up of inflatable material, and multiple compartments (with or without valve systems) can be used for height adjustment. In some embodiments, one or more zippers can be used for height adjustments (similar to height adjustment zippers in luggage). In one case a footstool cover can accept an inflatable bag which, when inflated, conforms to the outer cover foot-stool shape. The advantage of this system is that one can use any inflatable bag (need not be custom made footstool shape), and the outer cover is washable. In this case some securing mechanisms can be put inside the cover that secures the inflatable bag at a few places. In one case one can just scoop the ambient air to inflate the footstool (much like a beach inflatable), and there can be a valve to let any excess air out while inserting/fitting the inflatable bag inside the outer cover. In one implementations, a detachable hand-pump similar to a blood pressure measurement device (for example, Medline Model: MDS91482) can be used to inflate and deflate an inflatable stool. Other inflation mechanisms can also be used.

Adjustable Platform Height

Figure 9A:
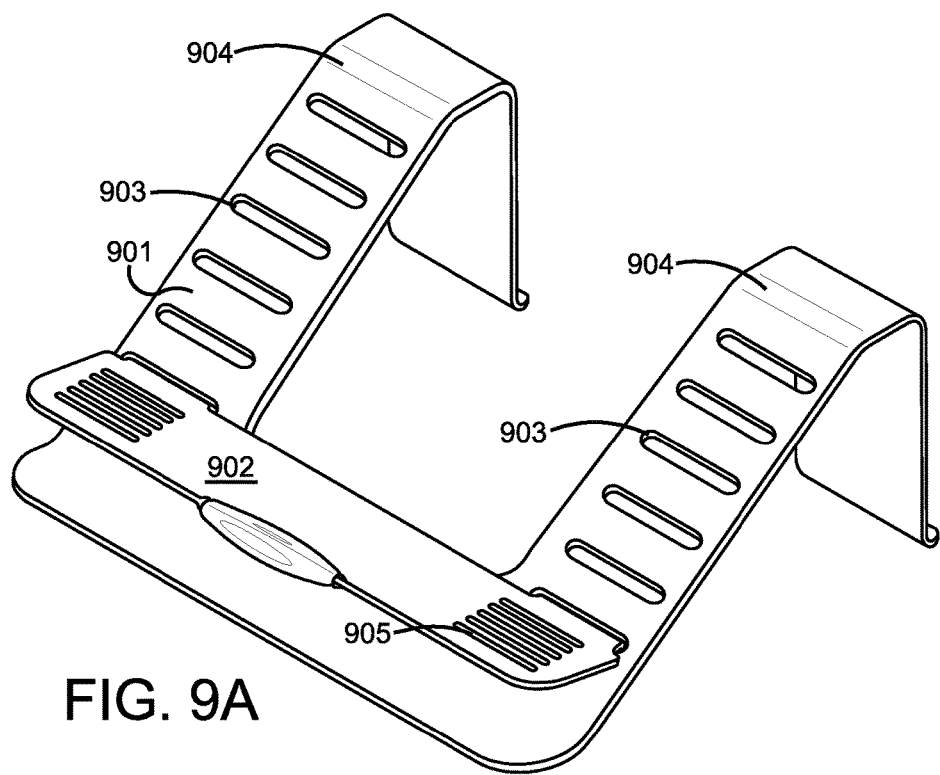
FIGS. 9A-9B illustrate an exemplary stool with an adjustable platform.
Figure 9B:
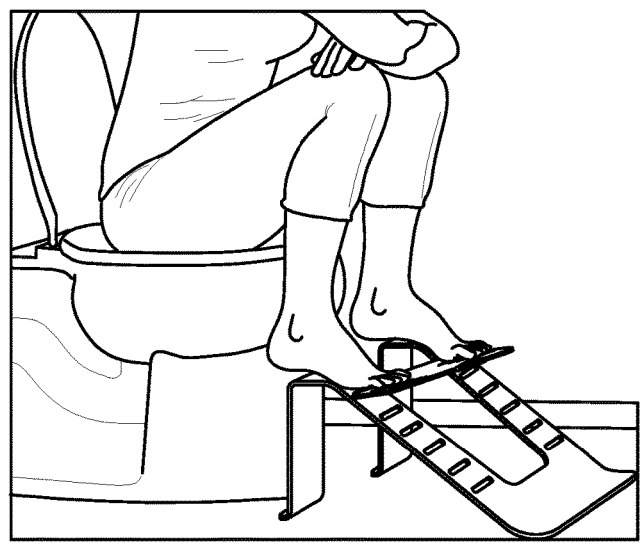

FIGS. 9A-9B illustrate an exemplary stool with an adjustable platform. The ramp design lends itself to easy height and squat adjustability in a manner that is not possible with a flat top footstool The exemplary stool in FIGS. 9A-B include ramp 901, platform 902, slots 903, an upper flat portion 904, and non-slip elements 905. Ramp 901 may extend in a downward slat from back to front, for example at an angle of 20, 25, 30, 35, 40 degrees or some other angle. Ramp 901 can receive a detachable platform 902. Platform 902 may be inserted into a pair of slots 903 on the ramp, wherein different slot pairs correspond to different heights for platform 902. Hence, by inserting the platform 902 in different slots 903 on ramp 901, the height of the platform 902 can be adjusted. The upper flat portion 904 can be used independent of the toe platform for a deep squat, and when platform 902 is inserted into the topmost slots of ramp 901, the stool of FIG. 9A acts like a flat-top footstool (see FIG. 9B). Platform 902, when inserted into a pair of slots 903, may rest at an angle with respect to a horizontal plane, such as for example 5, 10, 15, or 20 degrees, or some other angle. Patterns 905 can be placed in the toe area for non-slip purposes. The slots 903 on the ramp 901 may also serve as non-slip surfaces.

A massager may be implemented in an edge or upper surface of platform 902 (as shown in FIG. 9A). In some implementations, a massage may also be implemented in an edge or upper surface the lower front surface of the stool of FIG. 9A.

One advantages of the stool design of FIG. 9A is that platform 902 can be height adjusted easily and on-the-fly without the need for any tools. In some implementations, to provide additional strength and support, a bracket/rod can be used on each side of the footstool that connects the ramp and a back leg, or platform and the ramp or a leg of the stool.

In one embodiment, the height adjustable stool (FIGS. 9A-B) can be made collapsible. Hence, hinges can be used to implement a collapsible mechanism, and brackets can be used for additional strength. For a collapsible stool, the ramp 901 can be disjoint (for more compactness) without needing a middle bridge portion that connects the two ramp portions, in which case the toe platform can position the two ramps.

Figure 10A:
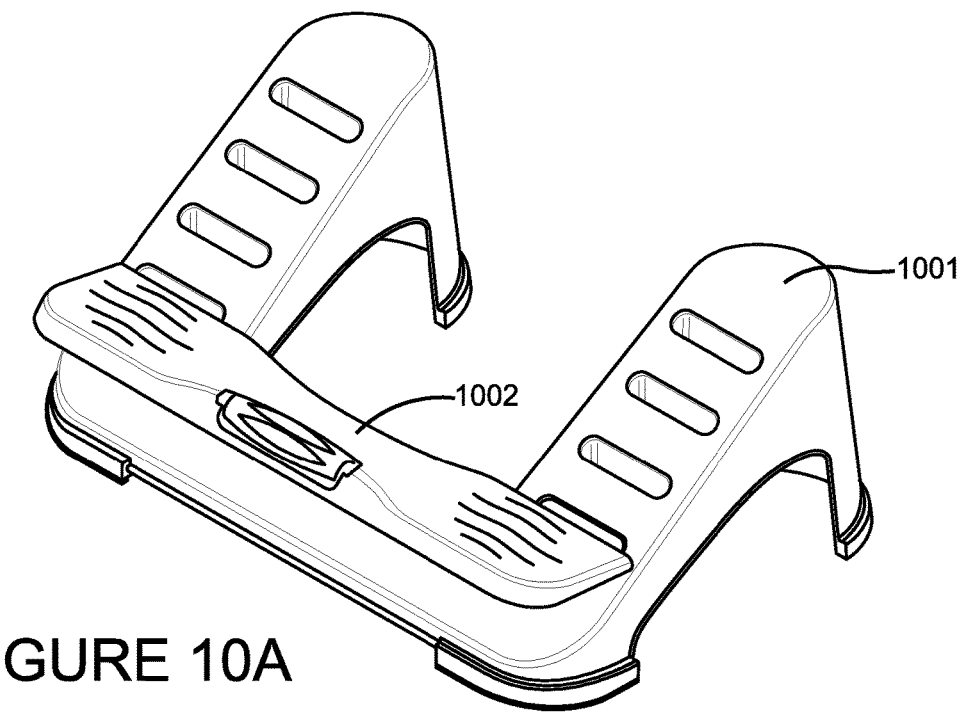
FIGS. 10A-10C illustrate another exemplary stool with an adjustable platform.
Figure 10B:
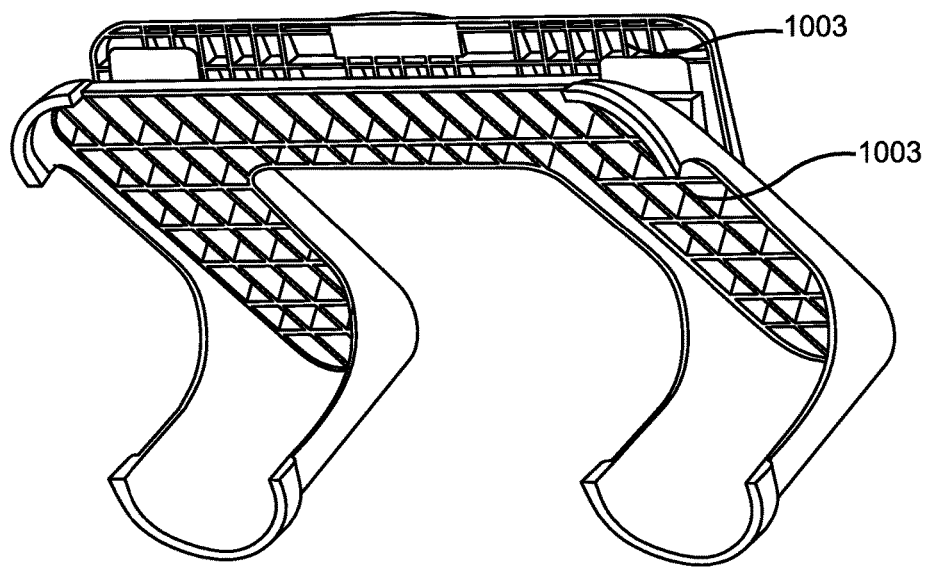
Figure 10C:
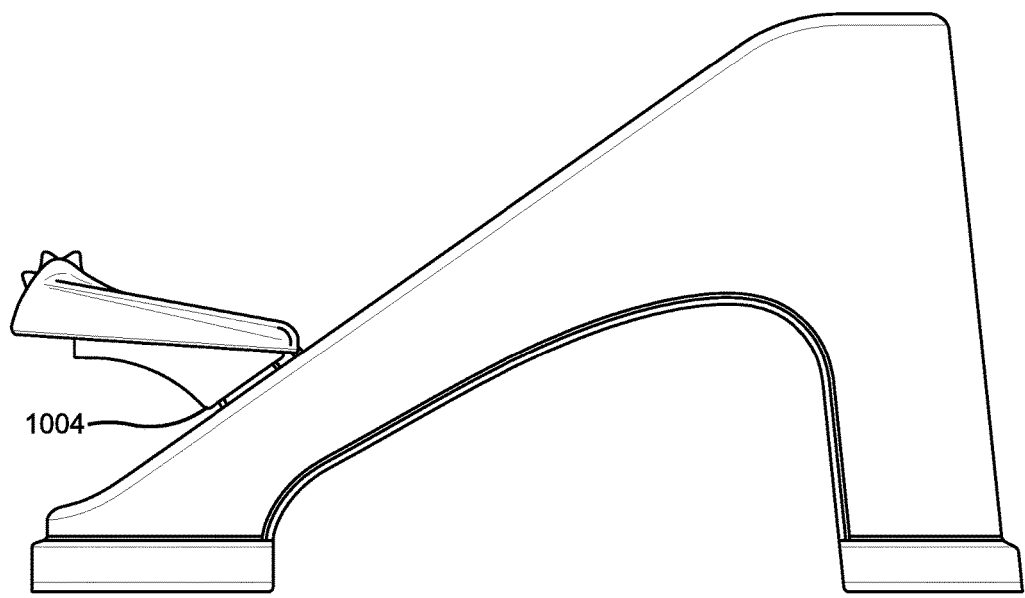

FIGS. 10A-C illustrate another exemplary stool with an adjustable platform. The stool of FIGS. 10A-C may be from a material such as a plastic. An exemplary stool of FIGS. 10A-C may include side walls 1001, platform 1002, ribs 1003, and brackets 1004. The stool of FIGS. 10A-C may also include reinforcements, for example a reinforcement element made of metal or other material, to strengthen the footstool. In some implementations, platform 1002 can be composed of plated/covered in of a premium material (e.g., carbon fiber, gold plated, wood, bamboo, etc.) for a desirable look and durability. Other materials may be utilized to make a stool with or without requiring design adjustments and without deviating from the main spirit of this concept.

The exemplary stool of FIGS. 9A-B or FIGS. 10A-C may include a rail system that allows a sliding height adjustment mechanism for the platform, as opposed to discrete changes in a slot-based adjustable height mechanism. Ability to adjust the platform height provides macro height adjustment capabilities for squatting, in addition to the micro height adjustment capabilities attainable my moving the feet forward or backward on the platform. This can be extremely useful for a household where the members are of very different heights, or for a user wanting to go from a relaxed sitting position, to a squatting position, or to deep squatting with ease.

Intelligent Foot Stool

The foot stool of the present technology may include computing elements such as memory, processors, controllers, sensors, input and output devices and ports, wireless communication systems, and other components that allow it to communicate with external objects, such as smart appliances, mobile applications, and back end server systems. This "intelligent" foot stool may also detect input locally, process the inputs, and perform tasks locally using output mechanisms incorporated into or communicatively coupled to the stool.

The intelligent features may be implemented in the stool in several ways. In some implementations, the intelligent features may be added to a stool through attachments. The attachments, including components that attach to the massage unit holder 104b, overlay units such as blanket or other unit that can be placed over the stool, and attachments such as feet pad attachments, may attach to the stool and provide intelligent features by themselves, in communication with a mobile application stored and executed on a mobile device (see FIG. 14), and in communication with other devices. Attachments that provide intelligent functionality to the stool are discussed below, including for example with respect to FIGS. 11-13. In some implementations, one or more intelligent features of the stool may be incorporated into the stool itself. An exemplary stool having one or more sensors and output devices providing intelligent capabilities to the stool is discussed below, including for example with respect to FIG. 14-15.

Figure 11:
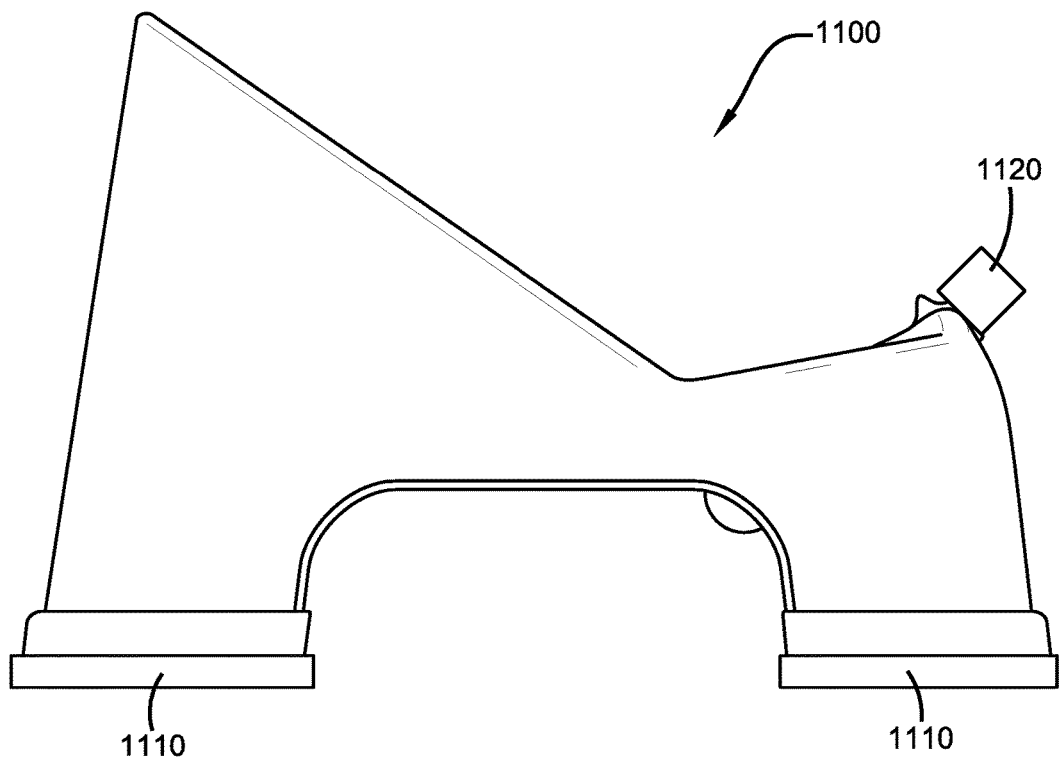
FIG. 11 illustrates an exemplary stool with an intelligent scale element.

FIG. 11 illustrates an exemplary stool with an intelligent scale element. The stool 1100 of FIG. 11 includes weight sensors 1110 (i.e., load cells) and processing circuitry 1120. The weight sensors may be designed to be placed on the legs, for example to replace one or more non-slide pads placed on the bottom of each stool leg, or elsewhere on the base of the stool such that the weight applied to the stool by a user can be captured by the one or more weight sensors. Each weight sensor may include a battery or other power source, logic circuitry, antennas, and other components to communicate with processing circuitry 1120 (e.g., to connect via RF wave communication such as a BLUETOOTH connection), Processor circuitry includes communication components to communicate with each weight sensor, logic to process received weight data from each sensor, and a display to output the user's weight. In some embodiments, the processor circuitry may communicate with a mobile device to capture a user's weight at a time specified by a user through a mobile application executing on the mobile device. The processor circuitry may be coupled to the stool via the massage unit holder 104b, in a manner similar to and in place of one or more massage units 104a.

The weight sensors may detect when a user first positions himself on the stool, and along with logic in the processing circuitry 1120 may determine the weight of a user at different times. For example, a weight may be captured for the user when the user first positions himself on the stool, and may continue to capture weight data for the user periodically until the user gets off the stool. In some instances, the weight of the user may be compared before and after the user performs a bowel movement.

Figure 12:
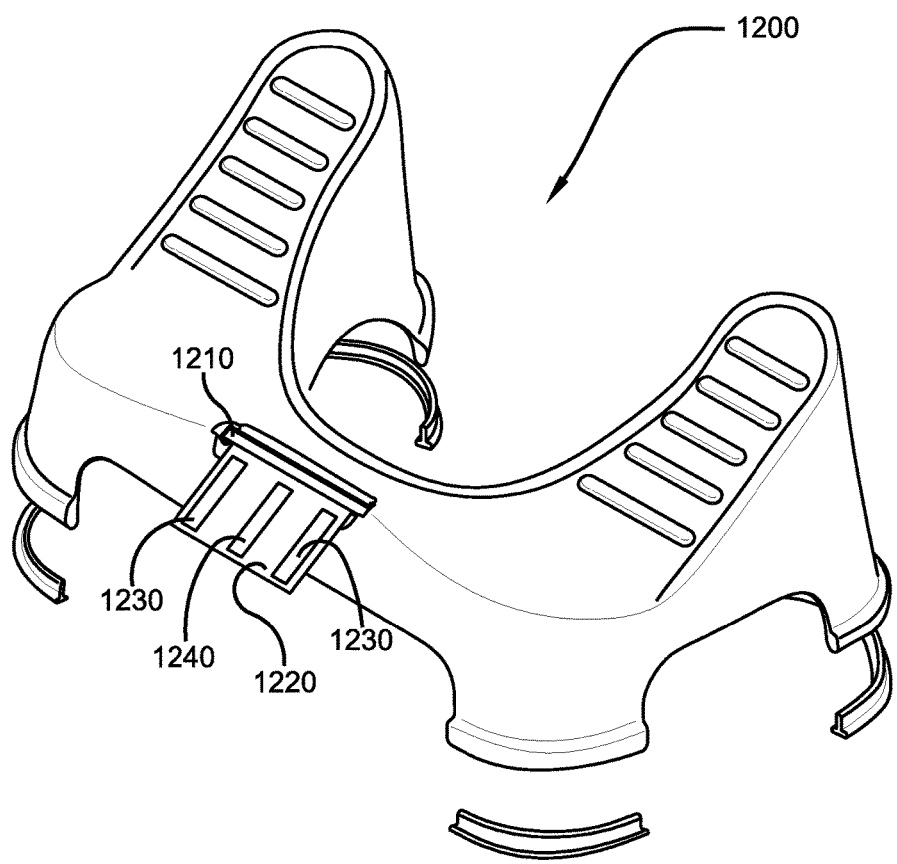
FIG. 12 illustrates an exemplary stool with an intelligent light and motion sensor element.

The current ramp design makes it easier for a user to stand upright on the stool compared to a flat-top footstool (lower center of gravity makes it more stable), and thus is ideal to integrate a smart scale unit. This provides a very easy and seamless way to keep track of one's weight on a regular basis FIG. 12 illustrates an exemplary stool with an intelligent light, ambient light sensor element, and motion sensor element. The stool 1200 of FIG. 12 includes an attachment component 1210, sensor housing 1220, sensors 1230, and light 1240 (e.g., ambient light 1240). In some implementations, the attachment component 1210 may attach to the stool using massage unit holder 104b.

The sensor housing 1220 may include a battery or other power source for powering the sensors, light and logic within sensor housing 1220. The sensor housing may include logic for receiving signals and processing the signals received from one or more lights and motion sensors 1230, one or more sensors, wired or wireless communication components, for example components for communicating via Bluetooth or Wi-Fi with a mobile application stored and executing on a mobile device.

Each of sensors 1230 may detect motion within the environment of the stool 1200. The sensors may be configured to detect motion in a particular direction, or may be adjustable so that one or more of the sensors may be directed to a particular direction. The light 1240 may include one or more lights for providing an illuminated space around the stool. Other lights can be incorporated into the stool, such as a light incorporated within attachment component 1210.

The motion sensors may be used with the logic within sensor housing 1220 to provide intelligent lighting capabilities. For example, when someone enters a bathroom, the motion sensor can detect the motion and, if minimum amount of light is not present in the bathroom, logic within the sensor housing can turn on one or more lights 1240. The night light intensity and/or color can adjust automatically based on the proximity of the user—if the user is far away it can be brighter to show the way, and as she or he approaches the toilet the light can dim.

In some implementations, one or more motion sensors and/or light sensors on the sensor housing can be mounted on an element that can be easily adjusted to point in the optimal direction (e.g., towards a bathroom entrance door). This adjustable direction feature can be helpful as different bathrooms have different positions and locations for a toilet. In some implementations, one or more light elements may be integrated into a massager unit itself, or the stool leg pad units.

The light elements 1240 also be controlled by a smartphone app (including, but not limited to, lighting features such as switch on/off, dim, change color, adjust direction, project images/movies, etc.). For example, a light may operate as a 'glow-in-the-dark' or similar element when attached to the footstool. In some implementations, a sensor housing may include more than one motion sensor and/or light sensor in order to detect motion and light levels in different locations and from different sources (e.g., the multiple sensors can cover multiple directions).

Figure 13:
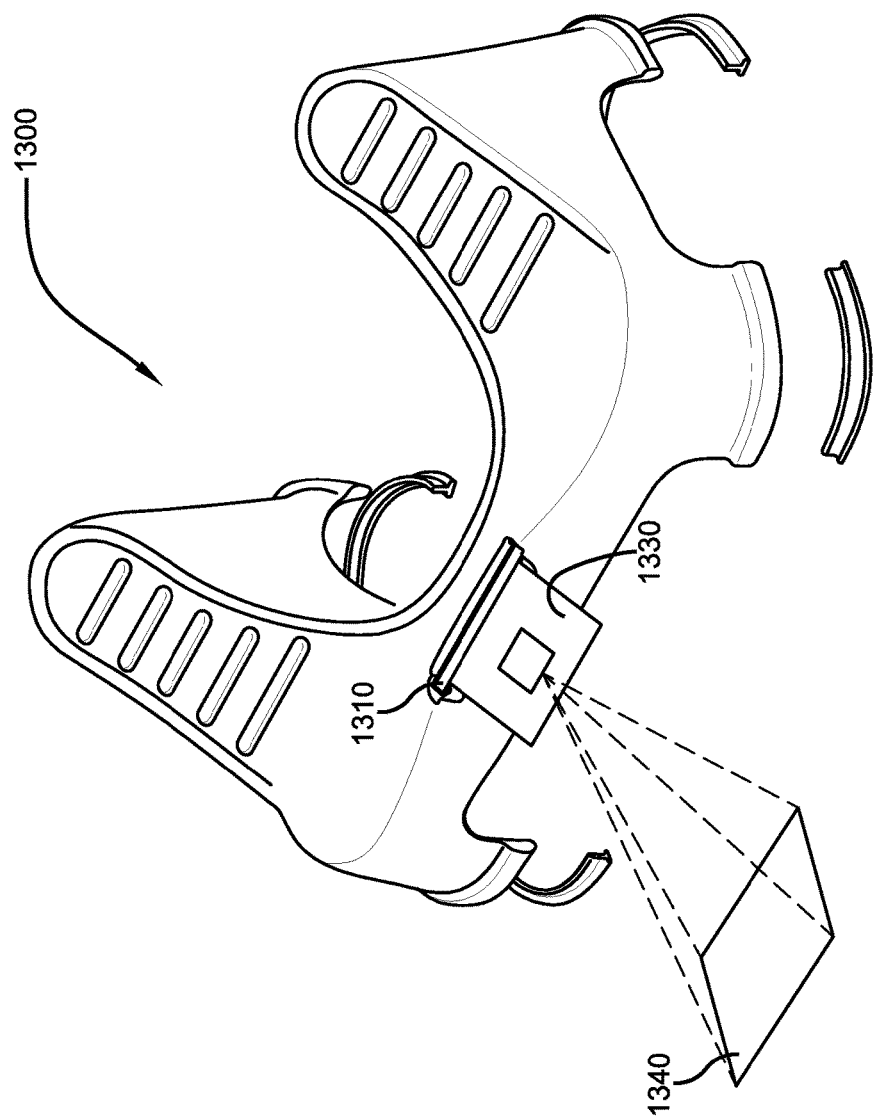
FIG. 13 illustrates an exemplary stool with an intelligent projector element.

FIG. 13 illustrates an exemplary stool with an intelligent projector element. The stool 1300 of FIG. 13 may include a connection element 1310, a projector housing 1320, and a projector 1330. The connector element 1310 may couple the projector and projector housing to the stool using the massage unit holder 104b.

Projector housing 1320 may include a power source such as a battery, logic for processing image, video, and graphic content, a wired and/or a wireless communication components for receiving and transmitting content to be projected, such as streaming videos, images, text, graphics and other content, one or more processors and memory, and other components typically found in projection systems. Projector 1330 may include a projector suitable for receiving content to project onto a floor, wall or other surface. The projector may be implemented with, for example, projector MM200 by 3M, projector PK-101 by Optima; projector MBP200 by Samsung, projector RIF6 Cube; AMAZ-PLAY from Amazon; a Holographic Laser Projection (or HLP) from Light Blue Optics, or other suitable projector.

When projector 1330 projects an image 1340 onto a floor in front of a user of the stool, the user may be required to slight lean forward while sitting on the toilet with his or her feet on the stool in order to see the projection 1340. By enticing the user to lean forward, the projection mechanism of the stool contributes to a forward leaning posture which applies pressure to the colon, thereby assisting with healthy bowel movement.

Figure 14:
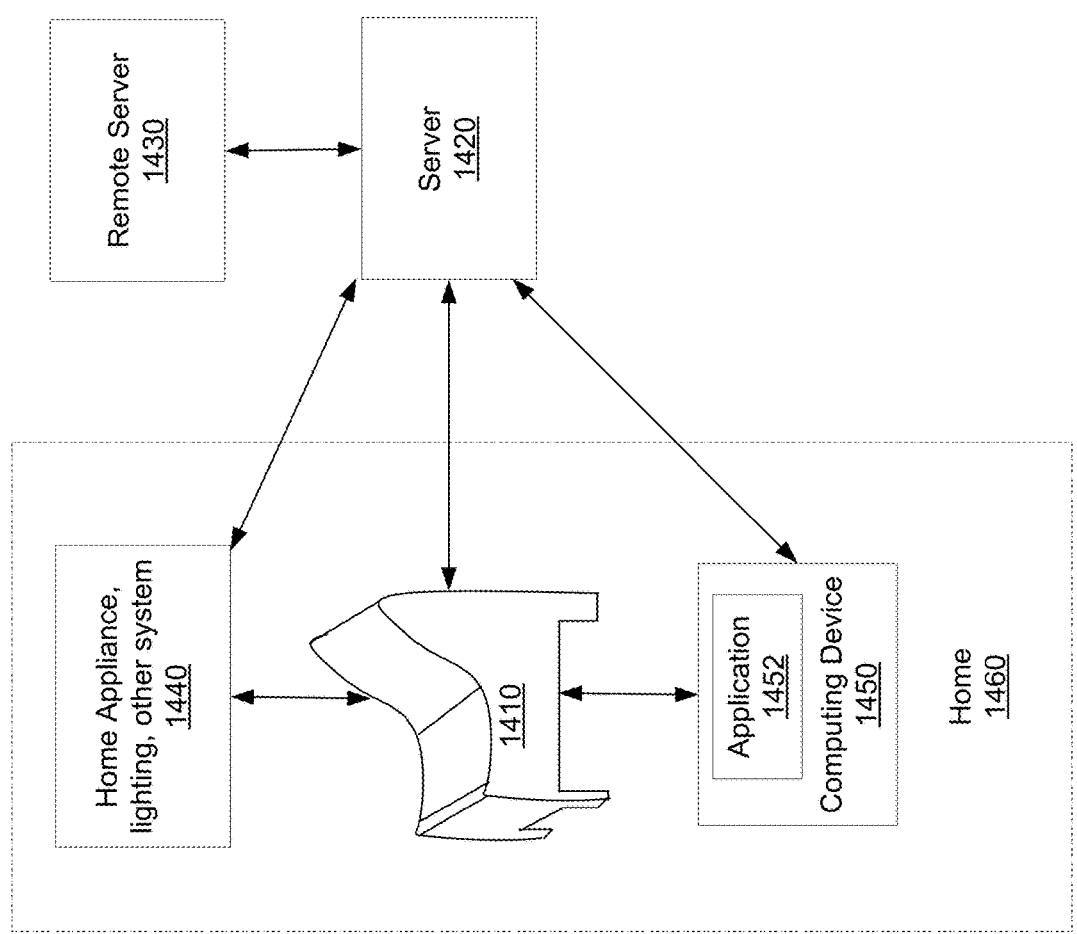
FIG. 14 illustrates a system for providing an intelligent stool that communicates with other devices.

FIG. 14 illustrates a system for providing an intelligent stool that communicates with other devices. The system of FIG. 14 includes an intelligent stool 1410, a server 1420, a remote server 1430, home appliance, lighting, or other home system or device 1440, and a computing device 1450. The intelligent stool 1410 may include one or more processors, memory, an input device, output device, and antennas and circuitry for commuting wirelessly. Intelligent stool 1410 may communicate with server 1420 over one or more networks, including a wireless network, cellular network, private network, public network, or other communication network. Intelligent stool 1410 is described in more detail with respect FIG. 15.

Server 1420 may communicate with intelligent stool 1410, computing device 1450, home appliance, lighting and other systems 1440, and remote server 1430 over one or more networks as described herein. Server 1420 may receive communications from intelligent stool 1410, process communications, and communicate with the stool 1410 itself or other devices. For example, server 1420 may receive data such as weight information, pulse information, fingerprint information, footprint information, and other data for a user positioned on the stool from intelligent stool 1410. Server 1420 may access one or more user accounts to determine if the received data matches that of an existing account. If so, preferences for the identified user counter provided back to intelligent stool 1410. The preferences may include audio preferences, video preferences, temperature preferences, massage preferences, and other data. Server 1420 may also communicate with systems provided by remote servers 1430. The services provided by one or more remote servers may include health services, calendar management services, news feeds, and other services.

Home appliance, lighting, and other home systems 1440 may include any system within a home that is accessible through a wireless network. Such systems may include appliances, lighting systems, watering systems, and other appliances. The systems 1440 maybe accessed and controlled by intelligent stool 1410 directly through a wireless connection such as a Wi-Fi connection, radio frequency signal such as a BLUETOOTH signal, or indirectly through server 1420. In some instances, intelligent stool 1410 may include policies and logic that sends instructions or otherwise controls home appliance, lighting, or other systems 1440 based on a recognized user, user activities and detected status while the user is positioned on intelligent stool 1410, or other events.

Computing device 1450 may include an application 1452. In some instances, computing device 1450 may include a smart phone and application 1452 may be implemented as a mobile app stored and executed on a smart phone. The application, when executed by one or more processors on computing device 1450, may control features and accessories of intelligent stool 1410. For example, application 1452, when executed, may provide an interface for controlling intelligent stool 1410 audio output, lighting, height, temperature, sensors such as pulse and moisture detection, and other aspects of intelligent stool 1410. In some instances, the intelligent stool, home appliance and other home systems, and the computing device may all be located within the vicinity of each other, such as for example within a particular home 1460.

Application 1452 may serve as a hub for smart devices—connecting the smart footstool and other smart devices (like smart water bottle, smart pedometer, etc.) and sharing data. For example, if the smart footstool finds someone sitting on the toilet for a long time struggling to perform a bowel movement, it can check when and how much water the user drank from the smart water bottle, and recommend drinking more water if needed. In some instances, if a smart water bottle finds the user is sitting on the toilet for too long and struggling to poop, then the water bottle can know that and increase the recommended water intake for the day. If a pedometer finds the user sitting on the toilet for too long, it can recommend the user to take frequent breaks from sitting on the chair (which can sometime cause constipation).

Figure 15:
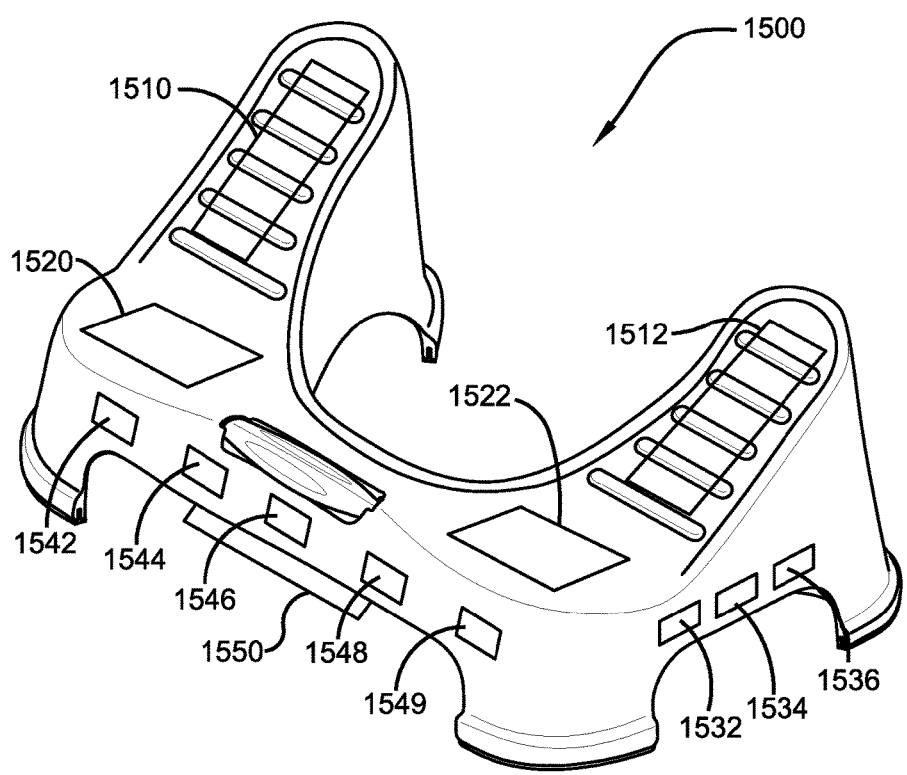
FIG. 15 illustrates an intelligent foot stool.

FIG. 15 illustrates an exemplary smart stool. Exemplary smart tool 1500 may include sensors 1510, 1512, 1520, 1522, 1532, 1536, 1542, 1544, 1548, and 1549, output devices 1534 and 1546, and circuitry 1550. Sensors 1510, 1512, 1520 and 1522 may detect information from a user's foot. For example, one or more of sensors 1510, 1512, 1520 and 1522 may be weight sensors to detect a user's weight, heart rate sensors to detect a user's heart rate, blood pressure sensors, hemoglobin sensors, temperature sensors, moisture sensors, or some other biological sensor. Each of sensors 1510, 1512, 1520, and 1522 may detect something from the user's foot (i.e., weight, presence, heart rate, blood pressure, hemoglobin, temperature, moisture) and communicate the data to circuitry 1550.

Sensors 1532, 1536, 1542, 1544, 1548, and 1549 may detect information from the environment in which the intelligent stool is positioned. For example, one or more sensors 1532-1549 may detect an environment temperature, light level, or motion. Each of sensors 1532-1549 may transmit a signal to circuitry 1550 based on the detected information in the local environment.

Output devices 1534 and 1546 are communicatively coupled to circuitry 1550 and may provide output based on input received through a sensor, logic within circuitry 1550, or some other event, such as an instruction or signal received from a remote mobile application. The output devices 1534 and 1546 may each include one or more of a steerable light, speaker, aroma or perfume dispenser, projector, display, or other output device. Though only two outputs are illustrated in FIG. 15, additional or fewer output devices may be incorporated onto stool 1500. For example, an output may be incorporated on a side of the stool opposite of output 1534, and one or more outputs may be incorporated into the rear vertical surface of the stool.

Circuitry 1550 may include one or more processors, memory, a wireless communication system, input components and output components. The circuitry may receive signals and data from sensors 1510, 1512, 1520, 1522, 1542, 1544, 1548, 1549, 1532 and 1536, process the signals and data, and provide an output signal for one or more of outputs 1546 and 1534. For example, circuitry may receive input from a motion sensor that motion is detected within the vicinity of the stool as well as input that there is a low light level in the area of the stool. The circuitry may receiving these sensor signals and generate a "night light" output through one or more of outputs (e.g., lighting elements such as LEDs) 1546 and 1534. Once a user's presence is detected on the stool through sensors 1510, 1512, 1520 and/or 1522, circuitry 1550 may dim the lights to provide a lower level of lighting.

The circuitry 1550 may receive input from one or more remote devices, such as a mobile application stored and executed on a remote device (e.g., application 1452 on device 1450). Circuitry 1550 may provide output such as music, video, lighting, or other output based on information received, for example through a wireless communication means such as Wi-Fi, from a remote device.

Circuitry 1550 may perform a variety of tasks based on input received from one or more sensors and/or a mobile application residing on a remote device. For example, circuitry within a foot stool may detect the time a user engages the foot stool, provide health monitor functions, provide a scale, perfume dispenser, intelligent massaging capability, projector and screen output, provide a virtual and/or intelligent assistant, and identify users of the stool. This and other functionality is described in more detail below.

Additional Stool Features

Implementations of the stool may utilize sensors and logic to implement different functions. For example, the sensors on the stool may include a timer, a footprint or touch sensor, a temperature sensor, a pulse detection sensor, and a moisture sensor. Each of the functions may be implemented by an accessory that is coupled to the stool, such as for example by coupling to the stool using the massage unit connector 104b, by one or more sensors, input devices, output devices, processors, memory, controllers, logic, circuitry, or other components built into the stool itself, via a cover or other unit that can be placed over or attached to an upper surface of the stool (or underneath the upper surface of the stool).

The timer may capture different time periods associated with the use of the stool by the user. For example, a pressure sensor may detect when a user sits on the stool, which may in turn start a timer. Different events may be captured by the stool and timestamps may be retrieved from the timer and stored for later processing. For example, time periods may be stored for the user such as a total time the user spent on the stool, the time between stool uses. And other time periods.

A footprint sensor or touch sensor may identify an area occupied by the user's foot on the surface of the stool. In some implementations, one or more surfaces of the stool, such as a ramp portion, a platform portion, bridge portion, and other portion, may include a touch input surface that detects the presence of a touch over many points on the corresponding surface. Level of detail for detecting touch points may be designed such that the footprint or touch sensor may detect a footprint of a user in enough detail to differentiate feet of different users. In some implementations, the stool may identify a user based on the user's footprint, area of foot, pressure applied, and other data collected by sensors on the stool. Different actions may be taken for the specific identified user, such as outputting music associated with the user's account, providing video, media, or other content through a display, wirelessly accessing other information, accounts, or data for the particular server, and other actions.

A temperature sensor may detect the temperature of the stool as well as the user's feet. When a user is detected to position herself on the stool, a temperature sensor may detect the temperature of the stool and warm the stool up to a particular temperature to make the stool a desired temperature. The desired temperature may be a default temperature, such as 70° F., or a temperature associated with a user account.

A pulse sensor may be implemented in the stool to detect a pulse of a user of the stool. The pulse sensor may be suitable to detect a pulse from a bottom of the user's foot, a side of the user's foot, or some other position of the user's foot positioned on or adjacent to the stool. A moisture sensor may be positioned at one or more locations on the stool. The moisture location may detect whether the user's foot is wet or dry, and may perform different actions based on the moisture detection. For example, if a user's foot is a slightly moist, the slight amount of moisture can be detected and interpreted to be sweat. When a sensor detects a slight amount of moisture, it may be determined the slight amount of moisture is due to stress of the user positioned on the stool. Based on the detection, steps may be taken to try and relax the user, such as for example automatically start a foot massage mechanism to massage the user's feet, play sounds that relax the user, play video on a display that relaxes the user, or other actions. If more than a slight amount of moisture is detected, the user's feet may be determined to be wet. In this case, the temperature of the surface on the stool which supports the user's feet may be increased, thereby helping dry the user's feet.

In some implementations, the stool may include an aroma release mechanism. The mechanism for releasing aromas may include a sonic diffuser for herbs that diffuse through pressure waves. The aroma release mechanism may be controlled by logic, for example in a controller coupled to the massager holder 104b, within the stool itself, or implemented in an application on a mobile device. The logic may control the aroma release mechanism to dispense aromas based on events such as when motion in the room is detected, periodically while a user is detected sitting on the stool, and when a user is detected to no longer be engaging the stool (i.e., sitting on the stool).

The stool may also include outputs such as speakers and a display device. The display may be tilted slightly forward to encourage a user leaning forward. Both the display and speakers may include one or more buttons on the stool to control the output, may provide an output based on logic contained within a processor within the stool, or may be controlled by a remote application running on a remote device.

The stool of the present technology may include a steaming mechanism. The steaming mechanism may include a water reservoir, a heater to heat the water in the reservoir, and the steam release mechanism. The steam release mechanism may release steam created by heating the water and the water reservoir to portions of the user's feet. In some instances, the steam may be released through tiny outlet pinholes underneath the feet and/or toes of the user, or may include one or more steam extension members that provide steam over an upper or side surface of the user's feet.

The stool may include one or more lights dispersed around an outer surface of the stool. The outer surface may be on the top, sides, or bottom of the stool. The lights may be used to automatically turn on when a user is detected to sit on the stool, provide soothing light treatments to the user while the user is using the stool on a toilet, provide a nightlight during dark conditions, and other light functions. The lights may be controlled by switches or inputs on the stool, a mobile device remote communication of the stool, a remote for the stool, or some other controlling mechanism. In some instances, the stool may control wirelessly controllable bathroom lights. For bathroom lights that may be controlled through a radio signal, the stool may dim or turn down the bathroom lights when the user sits on the stool and turn on the soothing light therapy on the stool while the user is positioned on the toilet and stool. When the user gets off this toilet and stool, the stool may turn off the soothing lights on the stool and turned the bathroom lights back on.

The stool may have one or more mechanisms for receiving external accessories. For example, the stool may include an attachment for receiving a magazine rack, stand, or other accessory for holding items a user may want to access while on the toilet.

The smart stool may perform several actions in response to data captured by one or more sensors. The smart stool may include a processor which receives sensor data, processes the data, and perform as one or more actions based on policies or rules applied to the sensor data. The actions may be performed through one or more accessories, such as for example one or more speakers, displays, heating actuators are elements, or other accessories built into the stool. For example, based on a particular weight, footprint, pulse, and other data, the stool may identify the particular user. Ranges of sensor data, such as pressure data, weight data, footprint data, pulse data, and optionally other data, may be stored in a user account for a user of the stool, either remotely or locally at the stool. Once a user is identified, one or more actions may be performed on the user based on user preferences. For example, the user's preferred massage may be applied to the user through surfaces or devices on the stool, preferred audio or video may be provided to the user while the users on the stool, the stool may be heated or cooled to a preferred temperature, and other actions may be performed.

In some instances, an application may communicate with a particular stool and control and/or communicate with components that implement a particular functionality. The application may be stored and executed on a mobile device, such as a smart phone, and may allow user to control aspects of the smart stool. For example, a user may control a massage being applied to the user's feet, the stool temperature, audio and video provided by the stool, and other aspects of the stool. In some instances, the stool of the present technology may be integrated into a toilet. In this implementation, upon detecting a user is sitting on the toilet, the stool may be automatically extended from the base of the toilet forward, to provide a platform for a user's feet to be positioned.

The massager unit (104a and 104b) can be multi-purpose and multi-functional, and because of the space above the platform and below the outer surface of the toilet bowel (see FIG. 6) there is ample space for such attachments/accessories. For example, instead of a massager unit, some other examples of attachments to couple to the stool at the massager connector 104b include but are not limited to a pouch for storing pedicure items, a foldable and retractable stand holder for smartphone/books/magazines, an adapter for accommodating one or more of these units.

In one case the footstool can receive and secure a fitted a cover, for example in the form of a fabric slip cover that is machine washable, a hard cover, or other configuration, with appropriate openings for attachments. There can be one cover for the whole footstool, one or more covers for portions of the foot stool such as a ramp.

In some implementations, the cover may include a massaging surface over one or more of platform 102 and ramp 101. In this case, the massage surface may massage the user's foot at one or more positions where the user's foot is detected to be present.

In some implementations, the cover can fit over an upper surface of the stool, such as for example a ramp portion 101 and platform 102. The cover may include a soft surface, may be temperature controllable, and may include one or more massaging elements within the cover. Heating elements and massaging elements implemented within the cover may be powered by a portable battery or standard outlet, may be controlled by one or more switches or inputs in the cover, logic within the stool, or remotely by a mobile device.

In some implementations, the cover can include liners and/or patches. The cover can include elements of a computing device, including but not limited to a processor, memory, controller, input devices, output devices, wireless and wired communication components. For example, the cover may include USB ports, SSD slots, and a BLE module, and so forth for external connection and data transfer.

In some implementations, the stool may include a dynamo that generates electricity when the user uses the massage roller. This electricity can power sensors, processors, memory, projectors, lighting, and other power driven electrical components incorporated in or added onto the stool, for example at a massager holder 104b. They dynamo may include a magnet attached to the base footstool, while the massager 104a can have wirings, or vice versa.

In some implementations, the stool may include a health and wellness mechanism which can be used in stand-alone mode or be connected to and controlled by a mobile application stored and executed on a mobile device. For example, when a user's foot is placed on a sensor implemented on the platform or ramp, the sensor may monitor the user and determine a heart rate, blood pressure, hemoglobin measurement, or other biological data. A display (on the stool, an attachment to the stool at the massager holder 104b, or a mobile application) can direct the user based on the application. For example, the display can show and direct the user to apply a specific amount of pressure with a specific part of the foot. Once that specific level of pressure is reached, the unit can record the blood pressure and provide the recorded blood pressure to the user via a display on the stool or a remote mobile device. The unit can have a smell sensor that can analyze the smell during using the toilet for diagnostics. The unit can have a timer that can record amount of time spent each day and the timing and frequency (and provide appropriate health or wellness related feedback for example).

In some implementations, the stool may include a personal assistance mechanism which can be used in stand-alone mode or can be connected to and controlled by a mobile application on a mobile device. The personal assistance mechanism can contain batteries, speakers, screens, projectors, clock/timer, wireless communication capability, sensors, controls for external devices, and so forth. In one example, after a user sits on the toilet and stool, the personal assistance mechanism can communicate with lights, door locks and other components in the bathroom that are wirelessly in communication with the personal assistance mechanism to close and lock the bathroom door, switch off the main light or dim it, and/or play some soothing/stress-relieving music or read the news headlines/important emails/weather reports/stock updates/short recaps or project video on a surface near the personal assistance mechanism. The personal assistance mechanism may include a voice recorder to record, store, and transmit dictation or other content by the user.

The bathroom is also a place when most people are relaxed, and offers a venue to serve short, targeted, and personalized ads/sponsored-content via a display in the personal assistance mechanism. In some implementations, a user can also make a phone call using the personal assistance mechanism while using the toilet. In one case the personal assistance mechanism can present contextually relevant information. For example, if a user's bowel movement is smelling unlike a typical bowel movement or has some other abnormality, the personal assistance mechanism can suggest some remedies for it, or if someone is sitting for too long and may be constipated it can remind to drink some water as well as suggest other remedies. In another example, as soon as a user is done using the toilet, the personal assistance mechanism can activate/arrange/make-ready the next task for the particular user, such as for example begin to heat a pot of coffee.

In some implementations, the personal assistance mechanism can have logic that processes sensor input to determine who is in the bathroom (from a user voice, noise, face-recognition, movement, foot print, breathing, etc. signature), and what he/she is doing in the bathroom (for example brushing sound, or in the shower sound, or from the personal history, etc.) and provide services accordingly. For example, a user may like to listen to news while using the toilet, listen to rock while brushing and classical while in the shower. The personal assistance mechanism may remind the user to moisturize-well after the shower based on the dryness/humidity/temperature outside, can pre-heat a toilet seat to a preferred temperature for the user, and once a shower is done the personal assistance mechanism can heat coffee or breakfast for the user. The personal assistance mechanism can tailor/customize different services for different users and activities (while in the bathroom).

In some implementations, the personal assistance mechanism can include, but is not limited to, a temperature sensor that can adjust the footstool to a comfortable temperature, a sweat sensors for diabetics and stress level diagnosis, a sonic diffuser for herbs (herbs diffuse by pressure waves, no need of shaking) used for therapeutic purpose, or a Wi-Fi connected small/micro/nano/pico projector gesture control.

The smart footstool can be personalized for each individual in a household, and accordingly process input from one or more sensors to determine what user is using the stool, what the user is doing or prefers, and provide a customized experience to the user. There are many ways the footstool can identify the current user of the footstool. In some implementations, a user can log in via smartphone for the footstool to communicate to the foot stool who the current user is. In some implementations, a footprint sensor can be used to identify the user, for example by identifying a toe print, an area of pressure points or surface contact by the user's foot, or other surface input received on the platform and/or ramp. In some implementations, the footstool can have distributed sensors on the surface that can determine who the user is (based on the user foot size for example) in a given household. In some implementations, the integrated scale can be used to determine the user based on the weight (in a household setting). In some implementations, the user can simply cycle through the list of users and choose himself or herself in a list of users registered with the particular stool (in a household setting). In some implementations, it can have a voice and/or sound recognition that can recognize the user based on typical sound/noise the user makes while in the bathroom. In some implementations, it can have a camera and face recognition that can recognize the user In some implementations, the footstool can communicate to the user via gentle vibration, oscillation, light, or other means. For example, if a user is attending the nature's call and reading a novel, and if he gets an important message or a call (or if someone else is waiting to use that bathroom, or whatever), it can gently notify the user by giving a gentle vibration, or light blink, etc.

In some instances, the ramp, platform, or other portions of the stool may have touch sensors that detect pressure such as "tapping" by a user's foot. Logic implemented by circuitry within the stool can perform different tasks based on the tapping. For example, detecting a single tap may cause audio to be output in speakers implemented within the stool. Detecting another single tap may cause the audio to stop. Detecting a double tap may cause the stool to detect the user's pulse and display the pulse through a display on the stool. Detecting a triple tap may cause the stool to perform a massaging sequence on the user's feet. Other actions may be associated with other variations of tapping or contact provided to the stool by the user.

The present technology has several advantages over devices of the prior art. The current technology combines the efficiency of the eastern toilet and convenience of the western toilet. The ramp induces a user to lean forward, thereby causing the legs to apply pressure to the user's stomach. The pressure may assist with forcing feces through the intestines and towards the bowels of the user. Squatting helps a colon align, and allows the user thigh to put pressure on the tummy. Both are good for good bowel movement. The raised ramp design facilitates both. The present device works for almost everyone, even for expecting mothers, elderlies, for those who are relatively short, and those who are not so flexible.

The ramp design provides a better foot entry/loading facility to the stool than the conventional flat top design. Because of the ramp design, a user does not have to lift their whole foot/leg, just raise the heels and then raise the toes just little bit to load the feet to the stool. Because of the flat region for the toes (on platform 102), one can easily adjust the toe position (forward or backward) to adjust the foot angle. Because of the ramp design, the center of gravity of the stool is lower (compared to the conventional designs with flat top), which helps achieve better stability. The front hump design provides facility for easy push/pull with the toes to be able to adjust the stool position (easily with the feet itself without having to use the hands. In addition the ramp design, the heel also provides an easy push facility with the foot. The approach angles of the hump and the ramp may be designed to facilitate easy push/pull with the feet.

The present device works for people of all heights because of the lower platform and ramp. The device allows for easy adjustment of knee height by easily adjusting the foot angle. If a user does not want to raise their knees, a user can keep their heels engaged on the platform area 102 (for just a little extra lift) and extend the feet forward.

Figure 16:
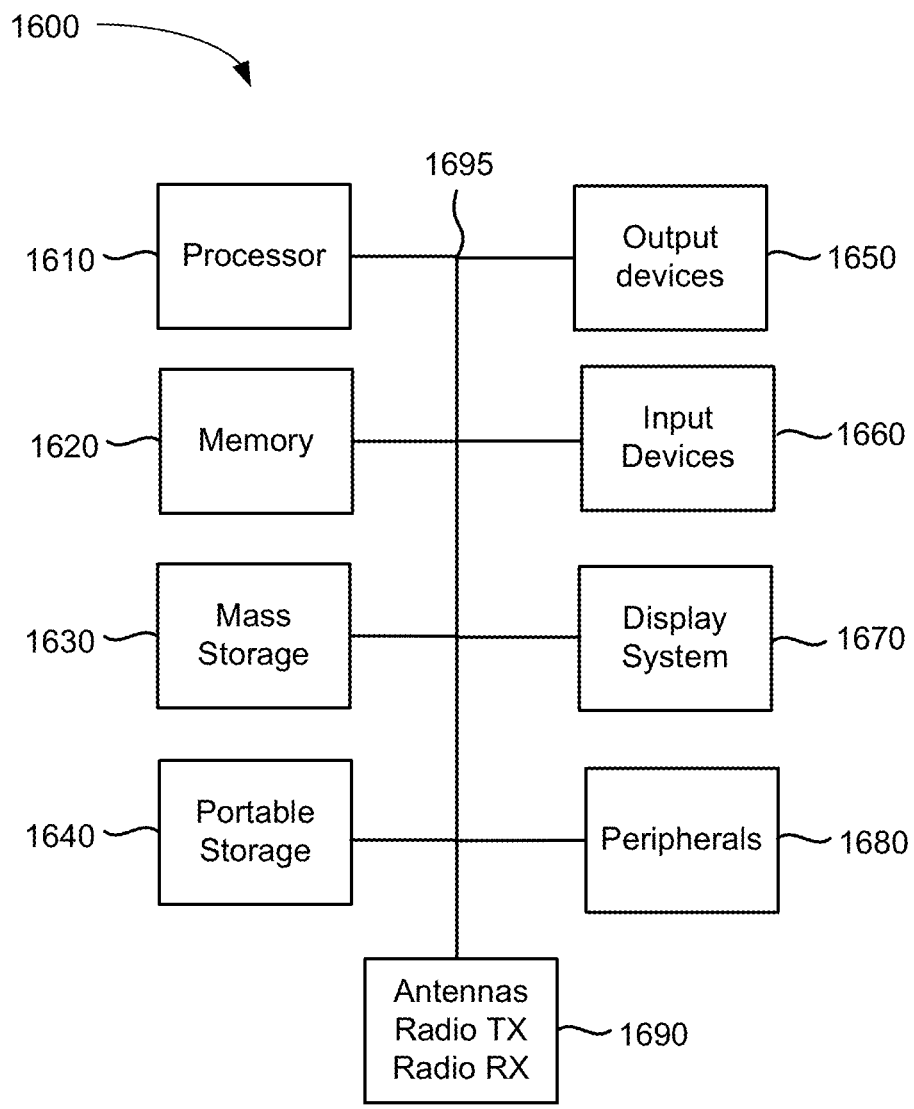
FIG. 16 is a block diagram of an exemplary computing device.

FIG. 16 illustrates an exemplary computing system 1600 that may be used to implement an embodiment of the present invention. System 1600 of FIG. 16 may be implemented in the contexts of the likes of home appliance, lighting or other system 1440, computing device 1450, server 1420 and remote server 1430. The computing system 1600 of FIG. 16 includes one or more processors 1610 and memory 1610. Main memory 1610 stores, in part, instructions and data for execution by processor 1610. Main memory 1610 can store the executable code when in operation. The system 1600 of FIG. 16 further includes a mass storage device 1630, portable storage medium drive(s) 1640, output devices 1650, user input devices 1660, a graphics display 1670, and peripheral devices 1680.

The components shown in FIG. 16 are depicted as being connected via a single bus 1690. However, the components may be connected through one or more data transport means. For example, processor unit 1610 and main memory 1610 may be connected via a local microprocessor bus, and the mass storage device 1630, peripheral device(s) 1680, portable storage device 1640, and display system 1670 may be connected via one or more input/output (I/O) buses.

Mass storage device 1630, which may be implemented with a magnetic disk drive or an optical disk drive, is a non-volatile storage device for storing data and instructions for use by processor unit 1610. Mass storage device 1630 can store the system software for implementing embodiments of the present invention for purposes of loading that software into main memory 1610.

Portable storage device 1640 operates in conjunction with a portable non-volatile storage medium, such as a floppy disk, compact disk, Digital video disc, solid state drive, or hard drive, to input and output data and code to and from the computer system 1600 of FIG. 16. The system software for implementing embodiments of the present invention may be stored on such a portable medium and input to the computer system 1600 via the portable storage device 1640.

Input devices 1660 provide a portion of a user interface. Input devices 1660 may include an alpha-numeric keypad, such as a keyboard, for inputting alpha-numeric and other information, or a pointing device, such as a mouse, a trackball, stylus, or cursor direction keys. Additionally, the system 1600 as shown in FIG. 16 includes output devices 1650. Examples of suitable output devices include speakers, printers, network interfaces, and monitors.

Display system 1670 may include a liquid crystal display (LCD) or other suitable display device. Display system 1670 receives textual and graphical information, and processes the information for output to the display device.

Peripherals 1680 may include any type of computer support device to add additional functionality to the computer system. For example, peripheral device(s) 1680 may include a modem or a router.

The components contained in the computer system 1600 of FIG. 16 are those typically found in computer systems that may be suitable for use with embodiments of the present invention and are intended to represent a broad category of such computer components that are well known in the art. Thus, the computer system 1600 of FIG. 16 can be a personal computer, hand held computing device, telephone, mobile computing device, workstation, server, minicomputer, mainframe computer, or any other computing device. The computer can also include different bus configurations, networked platforms, multi-processor platforms, etc. Various operating systems can be used including Unix, Linux, Windows, Macintosh OS, Android, and other suitable operating systems.

The foregoing detailed description of the technology herein has been presented for purposes of illustration and description. It is not intended to be exhaustive or to limit the technology to the precise form disclosed. Many modifications and variations are possible in light of the above teaching. The described embodiments were chosen in order to best explain the principles of the technology and its practical application to thereby enable others skilled in the art to best utilize the technology in various embodiments and with various modifications as are suited to the particular use contemplated. It is intended that the scope of the technology be defined by the claims appended hereto.

What is claimed is:

1. A foot stool, comprising:
   a platform, wherein the platform includes front and rear edges;
   a first ramp element and a second ramp element, the first and second ramp elements each coupled to the rear edge of the platform and each extending away from the platform at a first angle, the ramp elements extending away from the platform at the same first angle, the first and second ramp elements coupled to the platform such that toes of the users feet rest on the platform, a heel of one of the user's feet rest on the first ramp, and a heel of the other user's foot rest on the second ramp, the first and second ramp displaced apart by a distance which allows at least a portion of a front of a toilet to protrude between the first ramp and the second ramp; and
   a first holder located at a location on the platform that is closer to the front edge of the platform than the rear edge of the platform to receive a first attachment, wherein the first holder comprises a lower end and an opened top end.

2. The foot stool of claim 1, wherein the platform is positioned at an angle of about 10 degrees with respect to a horizontal plane.

3. The foot stool of claim 1, wherein the first ramp element and the second ramp element are positioned at an angle of about 35 degrees with respect to a horizontal plane.

4. The foot stool of claim 1, wherein the platform includes a non-slip element on the surface of the platform.

5. The foot stool of claim 1, wherein the first ramp element and the second ramp element each include a non-slip element on the surface of the ramp.

6. The foot stool of claim 1, wherein the first holder is located at the front edge of the platform.

7. The foot stool of claim 1, wherein the first attachment is a massager.

8. The foot stool of claim 7, wherein the massager is a rolling massager.

9. The foot stool of claim 7, wherein the massager includes a light.

10. The foot stool of claim 1, further comprising a second holder, wherein the second holder is configured to detachably receive a second attachment for storing the second attachment.

11. The foot stool of claim 1, further comprising:
    a first back leg pivotally connected to the first ramp element;
    a second back leg pivotally connected to the second ramp element; and
    first and second front legs pivotally connected to the platform, wherein the foot stool may be place in a folded state in which the first and second front legs are folded toward each other against the platform, the first back leg is folded along the first ramp, the second back leg is folded along the second ramp, and the platform is folded on the first and second ramps.

12. The foot stool of claim 1, further including a plurality of legs and weight sensors, wherein the weight sensors are placed on the bottom of the legs, wherein the weight sensors are configured to measure the user's weight or weight distribution on the legs that are different.

13. The foot stool of claim 1, wherein each of the ramp elements extends away and upwardly from the platform at a first angle with respect to a horizontal plane, wherein the platform is horizontal or slopes downwardly in the direction towards the ramp elements.

14. A foot stool, comprising:
    a platform;
    a first ramp element and a second ramp element, the first and second ramp elements each coupled to the platform and each extending away from the platform at a first angle, the ramp elements extending away from platform at the same first angle, the first and second ramp elements coupled to the platform such that toes of the users feet rest on the platform, a heel of one of the user's feet rest on the first ramp, and a heel of the other user's foot rest on the second ramp, the first and second ramp displaced apart by a distance which allows at least a portion of a front of a toilet to protrude between the first ramp and the second ramp;
    a first back leg pivotally connected to the first ramp element;
    a second back leg pivotally connected to the second ramp element; and
    first and second front legs pivotally connected to the platform, wherein the foot stool may be place in a folded state in which the first and second front legs are folded toward each other against the platform, the first back leg is folded along the first ramp, the second back leg is folded along the second ramp, and the platform is folded on the first and second ramps.

15. The foot stool of claim 14, wherein each of the ramp elements extends away and upwardly from the platform at a first angle with respect to a horizontal plane, wherein the platform is horizontal or slopes downwardly in the direction towards the ramp elements.

16. A foot stool, comprising:
    a platform, wherein the platform includes front and rear edges;

a first ramp element and a second ramp element, the first and second ramp elements each coupled to the rear edge of the platform and each extending away from the platform at a first angle, the ramp elements extending away from the platform at the same first angle, the first and second ramp elements coupled to the platform such that toes of the users feet rest on the platform, a heel of one of the user's feet rest on the first ramp, and a heel of the other user's foot rest on the second ramp, the first and second ramp displaced apart by a distance which allows at least a portion of a front of a toilet to protrude between the first ramp and the second ramp; and a first holder located at a location on the platform that is closer to the front edge of the platform than the rear edge of the platform to receive a first attachment, wherein the first attachment is a massager, wherein the massager includes a light.

\* \* \* \* \*